(12) United States Patent
Jouvenot et al.

(10) Patent No.: US 9,921,154 B2
(45) Date of Patent: Mar. 20, 2018

(54) MULTIPLEXED DIGITAL ASSAYS

(71) Applicant: Bio-Rad Laboratories, Inc., Hercules, CA (US)

(72) Inventors: Yann Jouvenot, Benicia, CA (US); Serge Saxonov, Oakland, CA (US); Simant Dube, Kirkland, WA (US); John Frederick Regan, San Mateo, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 889 days.

(21) Appl. No.: 14/099,750

(22) Filed: Dec. 6, 2013

(65) Prior Publication Data

US 2014/0171341 A1 Jun. 19, 2014
US 2017/0205345 A9 Jul. 20, 2017

Related U.S. Application Data

(63) Continuation-in-part of application No. 13/424,304, filed on Mar. 19, 2012, now Pat. No. 9,222,128, and a continuation-in-part of application No. 13/548,062, filed on Jul. 12, 2012, now Pat. No. 8,951,939.

(60) Provisional application No. 61/454,373, filed on Mar. 18, 2011, provisional application No. 61/507,082, filed on Jul. 12, 2011, provisional application No. 61/510,013, filed on Jul. 20, 2011, provisional application No. 61/734,296, filed on Dec. 6, 2012.

(51) Int. Cl.
*G01N 33/48* (2006.01)
*G01N 33/50* (2006.01)
*G01N 21/64* (2006.01)
*G06F 19/18* (2011.01)
*G06F 19/12* (2011.01)

(52) U.S. Cl.
CPC ............ *G01N 21/64* (2013.01); *G06F 19/12* (2013.01); *G06F 19/18* (2013.01)

(58) Field of Classification Search
None
See application file for complete search history.

(56) References Cited

U.S. PATENT DOCUMENTS

| 5,304,810 | A  | * | 4/1994  | Amos ................... 250/458.1 |
| 6,020,141 | A  |   | 2/2000  | Pantoliano et al. |
| 7,801,226 | B2 |   | 9/2010  | Suh et al. |
| 8,148,515 | B1 |   | 4/2012  | Mao et al. |
| 8,951,939 | B2 |   | 2/2015  | Saxonov et al. |
| 9,156,010 | B2 |   | 10/2015 | Colston, Jr. et al. |
| 9,222,128 | B2 |   | 12/2015 | Saxonov et al. |

(Continued)

FOREIGN PATENT DOCUMENTS

| AU | 2012231098     | 1/2017 |
| WO | 03064691 A2    | 8/2003 |

(Continued)

OTHER PUBLICATIONS

Ottesen et al. Microfluidic digital PCR enables multigene analysis of individual environmental bacteria. Science, 2006, vol. 314, pp. 1464-1467.*

(Continued)

*Primary Examiner* — Russell S Negin
(74) *Attorney, Agent, or Firm* — Kolisch Hartwell, P.C.

(57) ABSTRACT

System, including methods and apparatus, for performing a multiplexed digital assay.

28 Claims, 15 Drawing Sheets

(56) References Cited

U.S. PATENT DOCUMENTS

| | | |
|---|---|---|
| 9,702,822 B2 | 7/2017 | Litterst et al. |
| 2005/0266448 A1 | 12/2005 | Hagiwara et al. |
| 2006/0078888 A1 | 4/2006 | Griffiths et al. |
| 2009/0069194 A1 | 3/2009 | Ramakrishnan |
| 2009/0239308 A1 | 9/2009 | Dube et al. |
| 2009/0311713 A1 | 12/2009 | Pollack et al. |
| 2010/0022414 A1 | 1/2010 | Link et al. |
| 2010/0092973 A1 | 4/2010 | Davies et al. |
| 2010/0173394 A1 | 7/2010 | Colston, Jr. et al. |
| 2010/0233686 A1 | 9/2010 | Higuchi et al. |
| 2010/0248385 A1 | 9/2010 | Tan et al. |
| 2010/0304978 A1 | 12/2010 | Deng et al. |
| 2011/0000560 A1 | 1/2011 | Miller et al. |
| 2011/0104686 A1 | 5/2011 | Litterst et al. |
| 2011/0159499 A1 | 6/2011 | Hindson et al. |
| 2011/0244455 A1 | 10/2011 | Larson et al. |
| 2011/0250597 A1 | 10/2011 | Larson et al. |
| 2012/0122714 A1 | 5/2012 | Samuels et al. |
| 2012/0164690 A1 | 6/2012 | Wang |
| 2012/0208241 A1 | 8/2012 | Link |
| 2012/0219947 A1 | 8/2012 | Yurkovetsky et al. |
| 2012/0220494 A1 | 8/2012 | Samuels et al. |
| 2012/0252015 A1 | 10/2012 | Hindson et al. |
| 2012/0264646 A1 | 10/2012 | Link et al. |
| 2012/0302448 A1 | 11/2012 | Hutchison et al. |
| 2012/0309002 A1 | 12/2012 | Link |
| 2012/0316074 A1 | 12/2012 | Saxonov |
| 2012/0322058 A1 | 12/2012 | Regan et al. |
| 2012/0329664 A1* | 12/2012 | Saxonov et al. ............ 506/9 |
| 2013/0017968 A1 | 1/2013 | Gurtner et al. |
| 2013/0040841 A1 | 2/2013 | Saxonov et al. |
| 2013/0059754 A1 | 3/2013 | Tzonev |
| 2013/0178378 A1 | 7/2013 | Hatch et al. |
| 2014/0057273 A1 | 2/2014 | Litterst et al. |

FOREIGN PATENT DOCUMENTS

| | | |
|---|---|---|
| WO | 2006002167 A2 | 1/2006 |
| WO | 2010036352 A1 | 4/2010 |
| WO | 2011100604 A2 | 8/2011 |
| WO | 2011143478 A2 | 11/2011 |
| WO | 2012129187 A1 | 9/2012 |
| WO | 2014031908 A1 | 2/2014 |

OTHER PUBLICATIONS

Vogelstein et al. Digital PCR. PNAS, vol. 96, 1999, pp. 9236-9241.*

Arya, Manit et al., "Basic principles of real-time quantitative PCR", Expert Review of Molecular Diagnostics, vol. 5, No. 2, 2005, pp. 209-219.

Beer, N. Reginald et al., "On-Chip, Real-Time, Single-Copy Polymerase Chain Reaction in Picoliter Droplets", Analytical Chemistry, vol. 79, No. 22, Nov. 15, 2007, pp. 8471-8475.

Bhagwat, Arvind A., "Simultaneous detection of *Escherichia coli* O157:H7, Listeria monocytogenes and Salmonella strains by real-time PCR", International Journal of Food Microbiology, vol. 84, 2003, pp. 217-224.

Butler, John M. et al., "Capillary electrophoresis as a tool for optimization of multiplex PCR reactions", Fresenius Journal Analytical Chemistry, vol. 369, 2001, pp. 200-205.

Cawthon, Richard M., "Telomere measurement by quantitative PCR", Nucleic Acids Research, vol. 30, No. 10, 2002, pp. 1-6.

Dube, Simant et al., "Mathematical Analysis of Copy Number Variation in a DNA Sample Using Digital PCR on a Nanofluidic Device", PLoS ONE, vol. 3, Issue 8, Aug. 2008, pp. 1-9.

Higuchi, Russell et al., "Simultaneous Amplification and Detection of Specific DNA Sequences", Biotechnology, vol. 10, Apr. 1992 pp. 1-5.

Higuchi, Russell et al., "Kinetic PCR Analysis: Real-time Monitoring of DNA Amplification Reactions", Biotechnology, vol. 11, Sep. 1993, pp. 1-5.

Hindson, Benjamin J. et al, "High-Throughput Droplet Digital PCR System for Absolute Quantitation of DNA Copy Number", Analytical Chemistry, vol. 83, 2011, pp. 8604-8610.

Hua, Zhishan et al., "Multiplexed Real-Time Polymerase Chain Reaction on a Digital Microfluidic Platform", Analytical Chemistry, vol. 82, No. 6, Mar. 15, 2010, pp. 2310-2316.

Lind, Kristina et al., "Combining sequence-specific probes and DNA binding dyes in real-time PCR for specific nucleic acid quantification and melting curve analysis", BioTechniques. vol. 40, No. 3, Mar. 2006, pp. 315-318.

Mao, Fei et al., "Characterization of EvaGreen and the implification of its physicochemical properties for qPCR applications", BMC Biotechnology, vol. 7, No. 76, Nov. 9, 2007, pp. 1-16.

Markey, Amelia L. et al., "High-throughput droplet PCR", Methods, vol. 50, Feb. 2, 2010, pp. 277-281.

Martin, Kendall J. et al., "Fungal-specific PCR primers developed for analysis of the ITS region of environmental DNA extracts", BMC Microbiology, vol. 5, No. 28, May 18, 2005, pp. 1-11.

McDermott, Geoffrey P. et al., "Multiplexed Target Detection Using DNA-Binding Dye Chemistry in Droplet Digital PCR", Analytical Chemistry, vol. 85, Nov. 3, 2013, pp. 11619-11627.

Pinheiro, Leonard B. et al., "Evaluation of a Droplet Digital Polymerase Chain Reaction Format for DNA Copy Number Quantification", Analytical Chemistry, vol. 84, Nov. 28, 2011, pp. 1003-1011.

Pohl, Gudrun et al., "Principle and applications of digital PCR", Expert Review of Molecular Diagnostics, vol. 4, No. 1, 2004, pp. 41-47.

Qin, Jian et al., "Studying copy number variations using a nanofluidic platform", Nucleic Acids Research, vol. 36, No. 18, Aug. 18, 2008, pp. 1-8.

Schaerli, Yolanda et al., "The potential of microfluidic water-in-oil droplets in experimental biology", Molecular BioSystems, vol. 5, Oct. 12, 2009, pp. 1392-1404.

Therianos, Stavros et al., "Single-Channel Quantitative Multiplex Reverse Transcriptase-Polymerase Chain Reaction for Large Numbers for Gene Products Differentiates Nondemented from Neuropathological Alzheimer's Disease", American Journal of Pathology, vol. 164, No. 3, Mar. 2004, pp. 795-806.

Todorov, Tihomir et al., "A Unified Rapid PCR Method for Detection of Normal and Expanded Trinucleotide Alleles of CAG Repeats in Huntington Chorea and CGG Repeats in Fragile X Syndrome", Molecular Biotechnology, vol. 45, Mar. 9, 2010, pp. 150-154.

Wang, Weijie et al., "DNA quantification using EvaGreen and a real-time PCR instrument", Analytical Biochemistry, vol. 356, Jun. 9, 2006, pp. 303-305.

Wu, Yajun et al., "Detection of olive oil using the Evagreen real-time PCR method", European Food Research and Technology, vol. 227, Feb. 13, 2008, pp. 1117-1124.

Ye, Shu et al., "An efficient procedure for genotyping single nucleotide polymorphism", Nucleic Acids Research, vol. 29, No. 17, 2001, pp. 1-8.

Zhong, Qun et al., "Multiplex digital PCR: breaking the one target per color barrier of quantitative PCR", Lab on a Chip, vol. 11, 2011, pp. 2167-2174.

Zimmermann, Bernhard G. et al., "Digital PCR: a powerful new tool for noninvasive prenatal diagnosis?", Prenatal Diagnosis, vol. 28, Nov. 10, 2008, pp. 1087-1093.

* cited by examiner

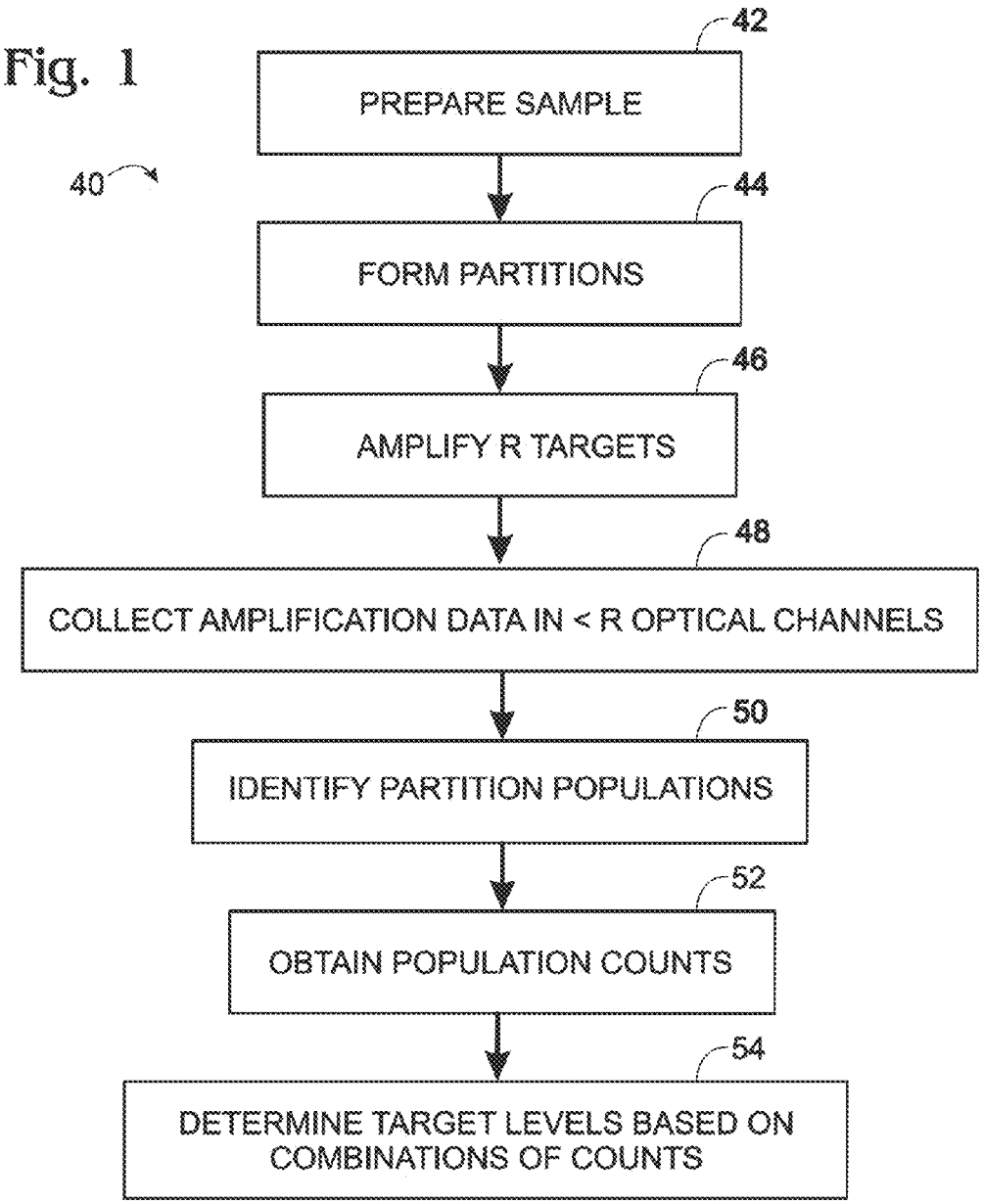
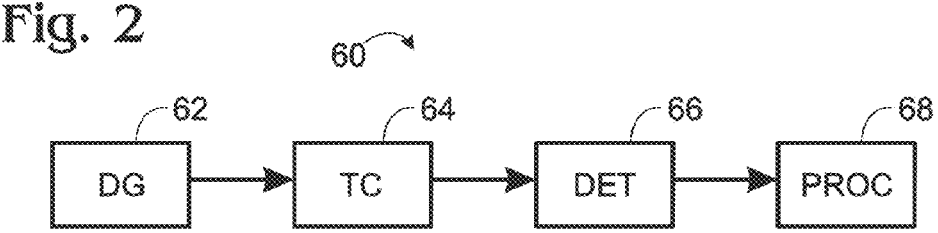

MULTIPLEXED DIGITAL ASSAYS

CROSS-REFERENCES TO PRIORITY APPLICATIONS

This application is a continuation-in-part of U.S. patent application Ser. No. 13/424,304, filed Mar. 19, 2012, and U.S. patent application Ser. No. 13/548,062, filed Jul. 12, 2012, and claims the benefit under 35 U.S.C. § 119(e) of U.S. Provisional Patent Application Ser. No. 61/734,296, filed Dec. 6, 2012.

U.S. patent application Ser. No. 13/424,304, in turn, is based upon and claims the benefit under 35 U.S.C. § 119(e) of U.S. Provisional Patent Application Ser. No. 61/454,373, filed Mar. 18, 2011.

U.S. patent application Ser. No. 13/548,062, in turn, is based upon and claims the benefit under 35 U.S.C. § 119(e) of U.S. Provisional Patent Application Ser. No. 61/507,082, filed Jul. 12, 2011; and U.S. Provisional Patent Application Ser. No. 61/510,013, filed Jul. 20, 2011.

Each of these priority applications is incorporated herein by reference in its entirety for all purposes.

CROSS-REFERENCES TO OTHER MATERIALS

This application incorporates by reference in their entireties for all purposes the following materials: U.S. Pat. No. 7,041,481, issued May 9, 2006; U.S. Patent Application Publication No. 2010/0173394 A1, published Jul. 8, 2010; U.S. Patent Application Publication No. 2012/0194805 A1, published Aug. 2, 2012; U.S. Patent Application Publication No. 2013/0084572 A1, published Apr. 4, 2013; and Joseph R. Lakowicz, PRINCIPLES OF FLUORESCENCE SPECTROSCOPY ($2^{nd}$ Ed. 1999).

INTRODUCTION

Digital assays generally rely on the ability to detect the presence or activity of individual copies of an analyte in a sample. In an exemplary digital assay, a sample is separated into a set of partitions, generally of equal volume, with each containing, on average, less than about one copy of the analyte. If the copies of the analyte are distributed randomly among the partitions, some partitions should contain no copies, others only one copy, and, if the number of partitions is large enough, still others should contain two copies, three copies, and even higher numbers of copies. The probability of finding exactly 0, 1, 2, 3, or more copies in a partition, based on a given average concentration of analyte in the partitions, is described by a Poisson distribution. Conversely, the concentration of analyte in the partitions (and thus in the sample) may be estimated from the probability of finding a given number of copies in a partition.

Estimates of the probability of finding no copies and of finding one or more copies may be measured in the digital assay. Each partition can be tested to determine whether the partition is a positive partition that contains at least one copy of the analyte, or is a negative partition that contains no copies of the analyte. The probability of finding no copies in a partition can be approximated by the fraction of partitions tested that are negative (the "negative fraction"), and the probability of finding at least one copy by the fraction of partitions tested that are positive (the "positive fraction"). The positive fraction or the negative fraction then may be utilized to determine the concentration of the analyte in the partitions by Poisson statistics.

Digital assays frequently rely on amplification of a nucleic acid target in partitions to enable detection of a single copy of an analyte. Amplification may be conducted via the polymerase chain reaction (PCR), to achieve a digital PCR assay. The target amplified may be the analyte itself or a surrogate for the analyte generated before or after formation of the partitions. Amplification of the target can be detected optically from a fluorescent probe included in the reaction. In particular, the probe can include a dye that provides a fluorescence signal indicating whether or not the target has been amplified.

A digital PCR assay can be multiplexed to permit detection of two or more different targets within each partition. Amplification of the targets can be distinguished by utilizing target-specific probes labeled with different dyes. However, instruments with more optical channels, to detect emission from an equivalent number of dyes, are more expensive than those with fewer channels. On the other hand, many applications, especially where sample is limited, could benefit greatly from higher degrees of multiplexing.

A new approach is needed to increase the multiplex levels of digital assays.

SUMMARY

The present disclosure provides a system, including methods and apparatus, for performing a multiplexed digital assay.

BRIEF DESCRIPTION OF THE DRAWINGS

FIG. 1 is a flowchart of an exemplary method of performing a multiplexed digital assay with more targets than optical channels for detection, in accordance with aspects of the present disclosure.

FIG. 2 is a schematic view of an exemplary apparatus for performing the multiplexed digital assay of FIG. 1, in accordance with aspects of the present disclosure.

FIG. 8 shows FAM intensities (top panel.

DETAILED DESCRIPTION

Figure 3:
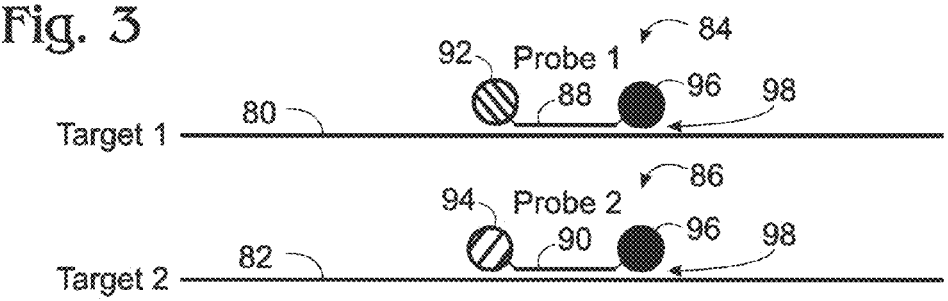
FIG. 3 is a schematic view of a pair of targets and corresponding probes capable of reporting the presence or absence of the targets via emitted light that may be detected together in the same channel for one or both targets in a multiplexed digital PCR assay, in accordance with aspects of the present disclosure.

The present disclosure provides a system, including methods and apparatus, for performing a multiplexed digital assay.

The present disclosure provides a system, including methods and apparatus, for performing a digital assay on a potentially greater number of targets through multiplexed detection of signals from reporters for two or more distinct targets in a common or shared channel ("the same optical channel"). The reporters may include the same fluorophore, such as FAM or VIC, or different fluorophores with similar spectral characteristics, so that light from two or more reporters can be collected simultaneously in the same optical channel. The assays may be constructed so that data for each target are distinguishable, for example, by choosing assays for each target that have sufficiently distinct endpoints (or time courses). The contents of each sample or sample partition may then be determined: those with no targets, those with a first assay (assay 1) target, those with a second assay (assay 2) target, and those with both, in a two-target assay. The total number of droplets positive for each target (e.g., target 1 and target 2) can be estimated by taking into account the number of droplets in each population. A concentration for each target may be estimated based on the number of droplets positive for each target and the total number of droplets, for example, using Poisson statistics. Moreover, the relative numbers of different targets (including reference targets) may be estimated, allowing determination of copy number (CN), copy number variation (CNV), and the presence/abundance of single nucleotide polymorphisms (SNPs), among other quantities. Copy number represents the number of copies of a given target present in a genome (e.g., humans have a diploid genome with a copy number of two for most autosomal genes). Copy number variation is a structural variation in the genome, such as deletions, duplications, translocations, and/or inversions, which may be a major source of heritable genetic variation, including susceptibility to disease (or disease itself) and responsiveness to disease treatment.

The assays may be extended in various ways. In some embodiments, the assays may involve detection of more than two targets in the same optical channel. For example, an assay for three targets may generate eight clusters or populations of data, separated by intensity. In the same or other embodiments, some targets may be analyzed in one channel (e.g., a FAM channel), and one or more other targets may be analyzed in one or more other channels (e.g., a VIC channel). Three targets, two in a first channel and one in a second channel, would again generate eight clusters or populations of data, but they would be separated in a two-dimensional intensity space and so in principle more easily resolvable.

A method of performing a multiplexed digital assay is provided. In the method, droplets may be formed that collectively contain R targets. The targets may be amplified in the droplets. Data may be collected that represents amplification of the targets in the droplets. The data may be collected in fewer than R optical channels. A level of each target may be determined with the data, wherein the level determined for at least one of the targets is based in part on a droplet count for a droplet population identified as positive for at least two of the targets.

Another method of performing a multiplexed digital assay is provided. In the method, droplets may be formed that collectively contain R targets, where R is at least three. A significant number of the droplets may contain a copy of each of two or more of the targets. The targets may be amplified in the droplets. Data may be collected representing amplification of the targets in the droplets. The data may be collected in fewer than R optical channels each representing a distinct waveband of emitted light. A plurality of droplet populations may be identified from the data, wherein forming, amplifying, and collecting are performed such that each droplet population positive for two of the targets is at least substantially resolved from each droplet population positive for only one of the targets. A level of each target may be determined based in part on one or more droplet populations identified as containing a pair of the targets.

Yet another method of performing a multiplexed digital assay is provided. In the method R targets may be amplified in droplets. Data representing amplification of the targets in the droplets may be collected. The data may be collected in a plurality of less than R optical channels each representing a distinct waveband of light. A plurality of droplet populations may be identified from the data, with each population containing a different combination of the targets. A level of each target may be determined. The step of determining for each target may be based on a value for droplet counts obtained from a combination of at least two droplet populations that excludes at least two other droplet populations.

Still another method of performing a digital assay is provided. In the method, droplets may be formed that collectively contain R targets and a probe corresponding to each target. R may be at least three, and each probe may include a different luminophore. The targets may be amplified in the droplets. Data may be collected that represents amplification of the targets in the droplets. The data may be collected in less than R optical channels each representing a distinct waveband of light. A level of each target may be determined based on the data.

Further aspects of the present disclosure are presented in the following sections: (I) system overview, and (II) examples.

I. System Overview

This section provides an overview of exemplary methods and apparatus for performing digital assays, in accordance with aspects of the present disclosure.

FIG. 1 shows a flowchart of an exemplary method 40 of performing a multiplexed digital assay. The steps presented for method 40 may be performed in any suitable order and in any suitable combination. Furthermore, the steps may be combined with and/or modified by any other suitable steps, aspects, and/or features of the present disclosure.

Sample preparation. A sample may be prepared for the assay, indicated at 42. Preparation of the sample may include any suitable manipulation of the sample, such as collection, dilution, concentration, purification, lyophilization, freezing, extraction, combination with one or more assay reagents, performance of at least one preliminary reaction to prepare the sample for one or more reactions in the assay, or any combination thereof, among others. Preparation of the sample may include rendering the sample competent for subsequent performance of one or more reactions, such as one or more enzyme catalyzed reactions and/or binding reactions.

In some embodiments, preparation of the sample may include combining the sample with reagents for amplification and for reporting whether or not amplification occurred. Reagents for amplification may include any combination of primers for the targets, dNTPs and/or NTPs, at least one enzyme (e.g., a polymerase, a ligase, a reverse transcriptase, a restriction enzyme, or a combination thereof, each of which may or may not be heat-stable), and/or the like. Accordingly, preparation of the sample may render the sample (or partitions thereof) capable of amplification of each of one or more targets, if present, in the sample (or a partition thereof). Reagents for reporting may include a different reporter for each target of interest. Accordingly, preparation of the sample for reporting may render the sample capable of reporting, or being analyzed for, whether or not amplification has occurred, on a target-by-target basis, and optionally the extent of any such amplification. The reporters each may be a labeled probe that includes a nucleic acid (e.g., an oligonucleotide) labeled with a luminophore (i.e., a photoluminescent moiety), such as a fluorophore.

Sample partitioning. The sample may be separated into partitions, indicated at 44. Separation of the sample may involve distributing any suitable portion including up to all of the sample to the partitions. Each partition may be and/or include a fluid volume that is isolated from the fluid volumes of other partitions. The partitions may be isolated from one another by a fluid phase, such as a continuous phase of an emulsion, by a solid phase, such as at least one wall of a container, or a combination thereof, among others. In some embodiments, the partitions may be droplets disposed in a continuous phase, such that the droplets and the continuous phase collectively form an emulsion.

The partitions may be formed by any suitable procedure, in any suitable manner, and with any suitable properties. For example, the partitions may be formed with a fluid dispenser, such as a pipette, with a droplet generator, by agitation of the sample (e.g., shaking, stirring, sonication, etc.), and/or the like. Accordingly, the partitions may be formed serially, in parallel, or in batch. The partitions may have any suitable volume or volumes. The partitions may be of substantially uniform volume or may have different volumes. Exemplary partitions having substantially the same volume are monodisperse droplets. Exemplary volumes for the partitions include an average volume of less than about 100, 10 or 1 µL, less than about 100, 10, or 1 nL, or less than about 100, 10, or 1 pL, among others.

The partitions, when formed, may be competent for performance of one or more reactions in the partitions. Alternatively, one or more reagents may be added to the partitions after they are formed to render them competent for reaction. The reagents may be added by any suitable mechanism, such as a fluid dispenser, fusion of droplets, or the like.

The partitions collectively, before amplification, may contain copies of a plurality of targets. Each partition may contain, on average, less than about five, four, three, or two copies, or less than about one copy of at least one target and/or of each target per partition. In any event, a significant number of the partitions (e.g., at least about 1%, 2%, 5%, 10%, or 20%, among others, of the partitions) may contain a copy of each of at least two targets, and/or a plurality of the partitions each may contain a copy of all targets.

The partitions when provided (e.g., when formed) may contain each target at "partial occupancy," which means that a subset (one or more) of the partitions contain no copies of the target and the rest of partitions contain at least one copy of the target. For example, another subset (one or more) of the partitions may contain a single copy (only one copy) of the target, and, optionally, yet another subset (one or more) of the partitions (e.g., the rest of the partitions) may contain two or more copies of the target. The term "partial occupancy" permits but does not require a dilution of the sample/reaction mixture providing the target, and is not restricted to the case where there is no more than one copy of the target in any partition. Accordingly, partitions containing the target at partial occupancy may, for example, contain an average of more than, or less than, about one copy, two copies, or three copies, among others, of the template/target per partition when the partitions are provided or formed. Copies of the target may have a random distribution among the partitions, which may be described as a Poisson distribution.

Target amplification. A plurality ("R") of targets may be amplified in the partitions. (R may be 2, 3, 4, or more than 4.) Amplification of each target may occur selectively (and/or substantially) in only a subset of the partitions, such as less than about one-half, one-fourth, or one-tenth of the partitions, among others. Amplification of each target may occur selectively in partitions containing at least one copy of the target (i.e., containing at least one copy of a template corresponding to the target).

Amplification may or may not be performed isothermally. In some cases, amplification in the partitions may be encouraged by heating the partitions and/or incubating the partitions at a temperature above room temperature, such as at a denaturation temperature, an annealing temperature, and/or an extension temperature, for one or a plurality of cycles. In some examples, the partitions may be thermally cycled to promote a polymerase chain reaction and/or ligase chain reaction. Exemplary isothermal amplification approaches that may be suitable include nucleic acid sequence-based amplification, transcription-mediated amplification, multiple-displacement amplification, strand-displacement amplification, rolling-circle amplification, loop-mediated amplification of DNA, helicase-dependent amplification, and single-primer amplification, among others.

Data collection. Amplification data may be collected, indicated at 48. The data may be collected in less than "R" optical channels. In other words, the number (R) of targets assayed may be greater than the number of optical channels used for detecting target amplification. In some cases, the data may be collected in only one or two optical channels, or in at least two, three, or more optical channels, among others.

An optical channel may represent a particular detection regime with which emitted light is generated and detected. The detection regime may be characterized by a waveband (i.e., a wavelength regime) for detection of emitted light. If pulsed excitation light is used in the detection regime to induce light emission, the detection regime may be characterized by a wavelength or waveband for illumination with excitation light and/or a time interval during which light emission is detected with respect to each light pulse. Accordingly, optical channels that are different from each other may differ with respect to the wavelength/waveband of excitation light, with respect to the wavelength/waveband of emitted light that is detected, and/or with respect to the time interval during which emitted light is detected relative to each pulse of excitation light, among others.

Data collection may include generating one or more signals representative of detected light. The signal may represent an aspect of light, such as the intensity of the light, detected in the same optical channel from reporters for two or more distinct targets. The signals optionally may include data collected in two or more different optical channels (e.g., in different wavelength ranges (wavebands) and/or color regimes) from reporters for the same and/or different targets). The light detected from each reporter may be light emitted from a luminophore (e.g., a fluorophore). The light detected in a given channel may be detected such that light from different reporters is summed or accumulated without attribution to a particular reporter. Thus, the signal for a given channel may be a composite signal that represents two, three, four, or more assays and thus two, three, four, or more targets.

The signal(s) may be created based on detected light emitted from one or more reporters in the partitions. The one or more reporters may report whether at least one of two or more particular amplification reactions represented by the signal has occurred in a partition and thus whether at least one copy of at least one of two or more particular targets corresponding to the two or more particular amplification reactions is present in the partition. The level or amplitude of the signal corresponding to the reporters may be analyzed to determine whether or not at least one of the particular amplification reactions has occurred and at least one copy of one of the particular targets is present. The level or amplitude of the signal may vary among the partitions according to whether at least one of the particular amplification reactions occurred or did not occur and at least one of the particular targets is present or absent in each partition. For example, a partition positive for a particular target may produce a signal level or amplitude that is above a given threshold and/or within a given range. Partitions may be analyzed and signals created at any suitable time(s). Exemplary times include at the end of an assay (endpoint assay), when reactions have run to completion and the data no longer are changing, or at some earlier time, as long as the data are sufficiently and reliably separated.

The reporters may have any suitable structure and characteristics. Each reporter may be a probe including an oligonucleotide and a luminophore associated with the oligonucleotide (e.g., with the luminophore covalently attached to the oligonucleotide), to label the oligonucleotide. The probe also may or may not include an energy transfer partner for the luminophore, such as a quencher or another luminophore. The probe may be capable of binding specifically to an amplicon produced by amplification of a target for the probe. The probe may or may not also function as a primer in the assay. Exemplary labeled probes include TaqMan® probes, Scorpion® probes/primers, Eclipse® probes, Amplifluor® probes, molecular beacon probes, Lux® primers, proximity-dependent pairs of hybridization probes that exhibit FRET when bound adjacent one another on an amplicon, QZyme® primers, or the like.

In some cases, at least one of the reporters may be a dye that interacts with (e.g., binds) nucleic acid relatively non-specifically. For example, the dye may not be attached to an oligonucleotide that confers substantial sequence binding specificity. The dye may be a major groove binder, a minor groove binder, an intercalator, or an external binder, among others. The dye may interact preferentially with double-stranded relative to single-stranded nucleic acid and/or may exhibit a greater change in a photoluminescent characteristic (e.g., intensity) when interacting with double-stranded relative to single-stranded nucleic acid. Exemplary dyes that may be suitable include luminescent cyanines, phenanthridines, acridines, indoles, imidazoles, and the like, such as DAPI, Hoechst® 33258 dye, acridine orange, etc. Exemplary intercalating dyes that may be suitable include ethidium bromide, propidium iodide, EvaGreen® dye, SYBR® Green dye, SYBR® Gold dye, and 7-aminoactinomycin D (7-AAD), among others.

Population identification. Partition populations each positive for a different combination of zero, one, or more of the R targets may be identified, indicated at 50. In some cases every combination of positives may be identified, and in other cases only a subset of all possible combinations may be identified (e.g., identifying single and double-positive populations, while ignoring rarer triple-positive and/or higher order populations.) Identification may be performed by a data processor using an algorithm (e.g., an algorithm that identifies patterns (e.g., droplets clusters) in the data), by a user, or a combination thereof. In some cases, a data processor may produce and output (e.g., display) a plot of the collected data (e.g., a 2-D scatter plot or histogram (e.g., see Examples 6 and 7), or, with three or more optical channels for detection, a series of 2-D scatter plots or histograms with different pairs of axes). The user then may define the boundary of each population based on the plot(s), e.g., through a graphical user interface to define population boundaries, and/or by inputting values (e.g., representing intensity ranges) to define a boundary for each population. Each population boundary may be defined by one or more ranges of values, a geometrical shape that surrounds the population (e.g., a polygon, ellipse, etc.), or the like.

Identification of partition populations may include assigning each partition to one of a plurality of predefined bins each corresponding to a distinct partition population.

The predefined bins may represent all possible combinations of positives for the target, or only a subset of the all possible combinations (e.g., where $N \geq 3$, all combinations of positives for zero, one, and two targets). Further aspects of population identification are presented below in Examples 6 and 7.

Obtain partition counts. A partition count for each partition population may be obtained, indicated at 52. The partition count may be a value representing the number of partitions constituting a particular partition population.

A number of partitions that are positive (or negative) for each target may be determined for the signal, indicated at 50. The signal detected from each partition, and the partition itself, may be classified as being positive or negative for each of the reactions/targets contributing to the signal. Classification may be based on the strength (and/or other suitable aspect) of the signal. If the signal/partition is classified as positive (+), for a given target, the reaction corresponding to that target is deemed to have occurred and at least one copy of the target is deemed to be present in the partition. In contrast, if the signal/partition is classified as negative (−), for a given target, the reaction corresponding to that target is deemed not to have occurred and no copy of the target is deemed to be present in the partition (i.e., the target is deemed to be absent from the partition). The data including all permutations of positives will generally fall into $2^N$ populations or clusters, where N is the number of targets, assuming that each population is distinguishable. Exemplary results for one, two, and three target systems in which data are collected in a single channel are shown in the following tables:

|  | Target A | Intensity |
| --- | --- | --- |
| Population 2 | + | Highest |
| Population 1 | − | Lowest |

|  | Target A | Target B | Intensity |
| --- | --- | --- | --- |
| Population 4 | + | + | Highest |
| Population 3 | + | − | Intermediate |
| Population 2 | − | + | Intermediate |
| Population 1 | − | − | Lowest |

|  | Target A | Target B | Target C | Intensity |
| --- | --- | --- | --- | --- |
| Population 8 | + | + | + | Highest |
| Population 7 | + | + | − | Intermediate |
| Population 6 | + | − | + | Intermediate |
| Population 5 | − | + | + | Intermediate |
| Population 4 | + | − | − | Intermediate |
| Population 3 | − | + | − | Intermediate |
| Population 2 | − | − | + | Intermediate |
| Population 1 | − | − | − | Lowest |

Determination of target levels. Levels of all of the targets may be determined, indicated at 54, based on various combinations of the counts obtained. Determination of target levels may (or may not) be based on each target having a Poisson distribution among the partitions. Each level may, for example, be a value representing the total number of partitions positive for the target, or a concentration value, such as a value representing the average number copies of the target per partition. The partition data further may be used (e.g., directly and/or as concentration data) to estimate copy number (CN) and copy number variation (CNV), using any suitable algorithms such as those described below and elsewhere in the present disclosure.

A level (e.g., concentration) of each target may be determined with Poisson statistics. The concentration may be expressed with respect to the partitions and/or with respect to a sample providing the target. The concentration of the target in the partitions may be calculated from the fraction of positive partitions (or, equivalently, the fraction of negative partitions) by assuming that copies of the target (before amplification) have a Poisson distribution among the partitions. With this assumption, the fraction f(k) of partitions having k copies of the template is given by the following equation:

$$f(k) = \frac{C^k}{k!} e^{-C} \quad (1)$$

Here, C is the concentration of the target in the partitions, expressed as the average number of target copies per partition (before amplification). Simplified Poisson equations may be derived from the more general equation above and may be used to determine target concentration from the fraction of positive partitions. An exemplary Poisson equation that may be used is as follows:

$$C = -\ln\left(1 - \frac{N_+}{N_{tot}}\right) \quad (2)$$

where $N_+$ is the total number of partitions (i.e., the partition count) positive for a given target, and where $N_{tot}$ is the total number of partitions that are positive or negative for the target. $N_{tot}$ is equal to a sum of (a) $N_+$ for the target and (b) the number of partitions negative for the target, or $N_-$. $N_+/N_{tot}$ (or $N_+/(N_++N_-)$ is equal to $f_+$, which is the fraction of partitions positive for the template (i.e., $f_+=f(1)+f(2)+f(3)+ \ldots$ ) (see Equation (1)), and which is a measured estimate of the probability of a partition having at least one copy of the template. Another exemplary Poisson equation that may be used is as follows:

$$C = -\ln\left(\frac{N_-}{N_{tot}}\right) \quad (3)$$

where $N_-$ and $N_{tot}$ are as defined above. $N_-/N_{tot}$ is equal to $f_-$, which is the fraction of negative partitions (or $1-f_+$), is a measured estimate of the probability of a partition having no copies of the target, and C is the target concentration as described above.

Equations (2) and (3) above can be rearranged to produce the following:

$$C=\ln(N_{tot})-\ln(N_{tot}-N_+) \quad (4)$$

$$C=\ln(N_{tot})-\ln(N_-) \quad (5)$$

The concentration of each target in a multiplexed assay can, for example, be determined with any of Equations (2)-(5), using values (i.e., partition counts) obtained for $N_{tot}$ and $N_-$ or $N_+$, for each target. In some cases, the value used for $N_{tot}$ (the total partition count) may be the same for each target. In other cases, the value used for $N_{tot}$ may vary, such as if some of the populations are excluded from the total count due to population overlap. In some embodiments, $N_{tot}$ may be equivalent to a combination of all populations, namely, a sum of the partition counts for all populations identified.

The value used for $N_-$ or $N_+$ is generally different for each target, and may result from summing the counts from a plurality of partition populations each containing a different combination of the targets being tested in the multiplexed assay. For example, with three targets (A, B, and C) in a multiplexed assay, the number of partitions positive for target A, $N_{+A}$, may be calculated as the sum of counts from the single (A only), double (AB and AC), and triple (ABC) positive populations, for use in Equation (2) or (4). Equivalently, the number of partitions negative for target A, $N_{-A}$, may be calculated, for use in Equation (3) or (5), as the difference between $N_{tot}$ and $N_{+A}$. Alternatively, the number partitions negative for A may be calculated as the sum of counts from each population that is negative for target A, namely, in this example, a triple negative ("empty") population, two single positive populations (B and C), and one double positive population (BC). The same process may be repeated for each of the other targets using partition counts from the appropriate subset of populations. In any event, determination of at least one target concentration and/or each target concentration may be based on a combination of counts from at least two populations and with the exclusion of at least two populations. In some cases, a combination of counts used for at least one target or for each target may include counts from only one-half of the populations.

In some embodiments, an estimate of the level of the template may be obtained directly from the positive fraction, without use of Poisson statistics. In particular, the positive fraction and the concentration (copies per partition) converge as the concentration decreases. For example, with a positive fraction of 0.1, the concentration is determined with Equation (2) to be about 0.105, a difference of only 5%; with a positive fraction of 0.01, the concentration is determined to be about 0.01005, a ten-fold smaller difference of only 0.5%. However, the use of Poisson statistics can provide a more accurate estimate of concentration, particularly with a relatively higher positive fraction, because the equation accounts for the occurrence of multiple target copies per partition.

Further aspects of sample preparation, partition formation, data collection, population identification, obtaining partition counts, and target level determination, among others, that may be suitable for the system of the present disclosure are described elsewhere in the present disclosure, such as below in Examples 5-7, and in the references identified above in the Cross-References, which are incorporated herein by reference.

FIG. 2 shows an exemplary system 60 for performing the digital assay of FIG. 1. System 60 may include a partitioning assembly, such as a droplet generator 62 ("DG"), a thermal incubation assembly, such as a thermocycler 64 ("TC"), a detection assembly (a detector) 66 ("DET"), and a data processing assembly (a data processor) 68 ("PROC"), or any combination thereof, among others. The data processing assembly may be, or may be included in, a controller that communicates with and controls operation of any suitable combination of the assemblies. The arrows between the assemblies indicate movement or transfer of material, such as fluid (e.g., a continuous phase of an emulsion) and/or partitions (e.g., droplets) or signals/data, between the assemblies. Any suitable combination of the assemblies may be operatively connected to one another, and/or one or more of the assemblies may be unconnected to the other assemblies, such that, for example, material/data are transferred manually.

Detector 66 may provide a plurality of optical channels in which data can be collected. The detector may have a distinct sensor or detection unit for each optical channel.

System 60 may operate as follows. Droplet generator 62 may form droplets disposed in a continuous phase. The droplets may be cycled thermally with thermocycler 64 to promote amplification of targets in the droplets. Signals may be detected from the droplets with detector 66. The signals may be processed by processor 68 to determine numbers of droplets and/or target levels, among others II. Examples This section presents selected aspects and embodiments of the present disclosure related to methods of performing multiplexed digital assays.

Example 1

Digital PCR Assays with Multiplexed Detection in the Same Channel

This example describes an exemplary digital PCR assay with multiplexed detection of two targets, using two probes, analyzed in the same channel. Other assays may involve three or more targets and three or more probes, where at least two targets are analyzed in the same channel.

FIG. 3 shows a pair of targets 80, 82 ("Target 1" and "Target 2") and corresponding probes 84, 86 ("Probe 1" and "Probe 2") that may be used to create a dedicated signal for each target in a digital PCR assay. Each probe may include an oligonucleotide 88, 90, a fluorophore 92, 94, and a quencher 96. Each of the fluorophore and the quencher may (or may not) be conjugated to the oligonucleotide by a covalent bond. The probe also or alternatively may include a binding moiety (a minor groove binder) for the minor groove of a DNA duplex, which may be conjugated to the oligonucleotide and which may function to permit a shorter oligonucleotide to be used in the probe.

Each oligonucleotide may provide target specificity by hybridization predominantly or at least substantially exclusively to only one of the two targets. Hybridization of the oligonucleotide to its corresponding target is illustrated schematically at 98.

Fluorophores 92, 94, which may be the same or different, create detectable but distinguishable signals in the same channel, allowing multiplexing in that channel. The signals may be distinguishable because an aspect of the fluorescence is different for one fluorophore than for the other fluorophore(s). For example, the intensity associated with one fluorophore, following reaction, may be lower or higher than the intensity(ies) associated with the other fluorophore(s). In some embodiments, one probe may be labeled with a different number of fluorophores than the other probe, and/or the probes may be located in slightly different local environments, creating a different level of fluorescence for each probe following reaction. Alternatively, or in addition, both probes may be labeled with the same number of fluorophores (e.g., one fluorophore), but there may be more or less of one probe than the other in the sample, so that a greater or smaller signal is created when the reactions have occurred. In some cases, the fluorophores themselves might be different, with one more or less intrinsically fluorescent than the other (e.g., due to differences in extinction coefficient, quantum yield, etc.), so long as each fluorophore can be detected in the same channel. Exemplary fluorophores that may be suitable include FAM, VIC, ROX, TAMRA, JOE, etc., among others.

Quencher 96 is configured to quench the signal produced by fluorophore 92 or 94 in a proximity-dependent fashion. Accordingly, light detected from the fluorophore may increase when the associated oligonucleotide 88 or 90 binds to the amplified target, to increase the separation between the fluorophore and the quencher, or when the probe is cleaved and the fluorophore and quencher become uncoupled during target amplification, among others. The quencher may be the same or different for each type of fluorophore. Here, the assay is designed so that the presence of a target gene leads to an increase in corresponding intensity, because amplification reduces quenching. In other assays, the reverse could be true, such that the presence of a target caused a decrease in corresponding intensity (although it typically is easier to detect a signal against a dark background than the opposite). Moreover, some embodiments may be constructed without a quencher, so long as the fluorescence and so the signal changes upon amplification.

Figure 4:
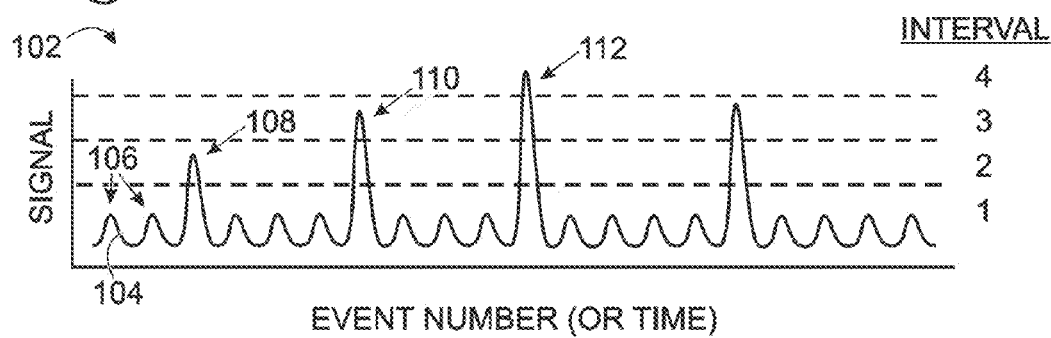
FIG. 4 is an exemplary graph showing a signal that may be created by detecting light emitted from the probes of FIG. 3 in a digital PCR assay performed in droplets, with the signal created by detecting light from each target together in the same optical channel from a fluid stream containing the droplets, in accordance with aspects of the present disclosure.

FIG. 4 shows an exemplary graph 102 of data corresponding to an exemplary digital PCR assay for Target 1 and Target 2 performed in droplets. The graph plots a signal 104 that represents light detected from probes 84, 86 (and/or one or more modified (e.g., cleavage) products thereof) (see FIG. 3). The signal is created from light detected over time in a single channel from a fluid stream containing the droplets and flowing through an examination region of the channel. The signal may be analyzed to determine whether neither Target, Target 1 alone, Target 2 alone, or both Targets 1 and 2 are present in each droplet. In particular, the strength or intensity of the signal in a system with two targets may be divided or thresholded into four intervals corresponding to no Target (Interval 1), Target 1 alone (Interval 2), Target 2 alone (Interval 3), or both Targets 1 and 2 (Interval 4):

Peaks 106 with maxima in Interval 1 correspond to droplets containing no Target (T1−/T2−). The measured signal corresponds to background (e.g., background fluorescence, scattering, etc.) and does not reflect the presence or amplification of either Target.

Peaks 108 with maxima in Interval 2 correspond to droplets containing Target 1 but not containing Target 2 (T1+/T2−). The measured signal corresponds to signal from Target 1 plus background and reflects amplification of Target 1 implying the presence of Target 1.

Peaks 110 with maxima in Interval 3 correspond to droplets containing Target 2 but not containing Target 1 (T1−/T2+). The measured signal corresponds to signal from Target 2 plus background and reflects amplification of Target 2 implying the presence of Target 2.

Peaks 112 with maxima in Interval 4 correspond to droplets containing both Targets 1 and 2 (T1+/T2+). The measured signal corresponds to signal from both Targets 1 and 2 plus background and reflects amplification of Targets 1 and 2 implying the presence of Targets 1 and 2.

In the present example, each droplet, whether positive or negative for each target, produces an increase in signal strength above the baseline signal that forms an identifiable peak 106, 108, 110, 112. Accordingly, the signal may vary in strength with the presence or absence of a droplet and with the presence or absence of a corresponding target.

The assignment of a droplet to a particular outcome (i.e., to one of T1−/T2−, T1+/T2−, T1−/T2+, and T1+/T2+) may be performed using any suitable algorithm. In the example above, peak heights (i.e., intensity values) associated with each outcome are sufficiently different that each can be unambiguously identified and assigned. Specifically, the peaks are assigned based on intervals delineated by values lying between (e.g., half way between) the peak heights for one outcome and the peak heights for adjacent outcomes. In other cases, the peak heights for each outcome may overlap at their extremes, so that thresholding may be neither simple nor linear. In such cases, statistical methods such as expectation maximization algorithms may be used to estimate the number of droplets or peaks associated with each outcome and the associated concentrations.

Example 2

Digital PCR Assay to Assess Copy Number of C61

Figure 5:
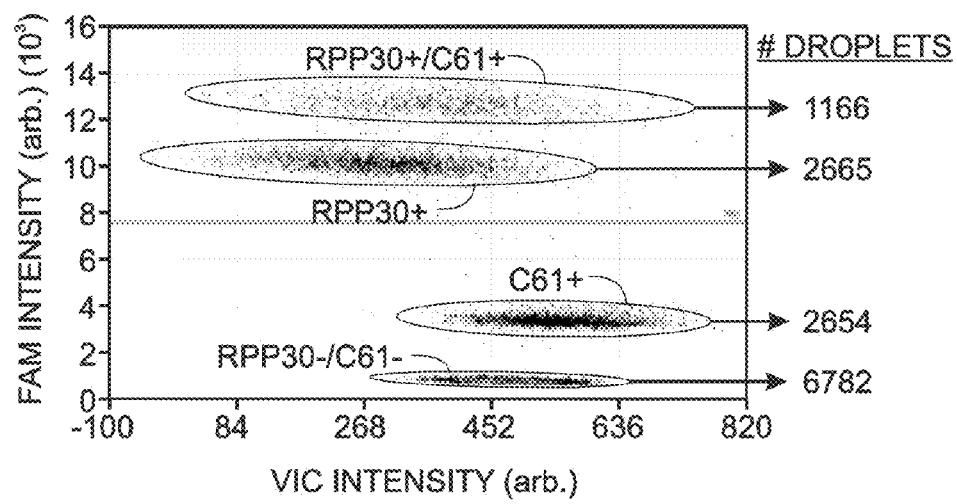
FIG. 5 is an exemplary scatter plot showing droplet (or peak) intensities in arbitrary units ("arb.") for a C61/RPP30 assay, where droplet data from reporters for C61 and RPP30 are collected together in the same optical channel and plotted as a function of intensity in a FAM channel (vertical axis) (configured to detect FAM-containing probes) versus intensity in a VIC channel (horizontal axis) (configured to detect VIC-containing probes).
Figure 6:
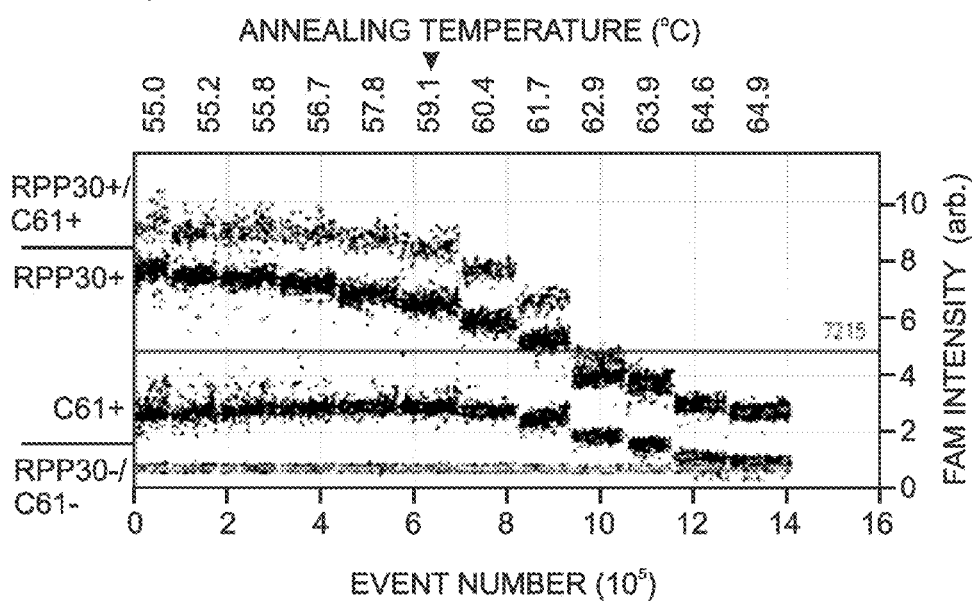
FIG. 6 is a graph showing FAM intensities for the C61/RPP30 assay of FIG. 5 for twelve different sets of assay conditions, namely, amplification of the C61 and RPP30 targets with different annealing temperatures (given in Celsius and denoted, from left to right, 55.0, 55.2, . . . , 64.6, and 64.9).

This example describes a first exemplary digital PCR assay, in which multiplexing in a single channel is used to assess copy number of the C61 gene; see FIGS. 5 and 6. Specifically, signals from two probes, one for the gene of interest, C61, and one for a reference gene, RPP30, are collected together, as a single signal, in a single channel and used to assess the number of copies of the gene of interest relative to the number of copies of the reference gene.

The principles described here may be used with any suitable gene(s). In this example, C61 is a gene of interest, for which information on copy number is sought, and RPP30 is a reference gene, which codes for ribonuclease P protein subunit p30, that is known to have two copies per genome.

The principles described here also may be extended to additional genes of interest, for example, two or three or more genes of interest, and may or may not involve reference genes such as RPP30. The number of copies may be determined absolutely, if the copy number of at least one of the genes (e.g., the reference gene) is known, or relatively, if the copy number of none of the genes is known.

FIG. 5 is a scatter plot showing data for the exemplary C61/RPP30 system. Specifically, FIG. 5 shows intensity in the FAM channel plotted as a function of intensity in the VIC channel for each droplet in a digital PCR assay. (Here and elsewhere in the present disclosure, the dots of a scatter plot represent individual droplets.) Visually, the data comprise four distinct populations, corresponding to four distinct ranges of FAM intensity (the intensities in the VIC channel are all low and overlapping). The assay is constructed so that amplification of C61 leads to a lower FAM intensity than amplification of RPP30 (although it would work as well if the reverse were true). The four populations may be summarized as follows:

Population 1, with the lowest FAM intensity, corresponds to droplets that are negative for RPP30 and C61 (i.e., droplets that did not include either gene).

Population 2, with the lower of two intermediate FAM intensities, corresponds to droplets that are positive for C61 and negative for RPP30 (i.e., droplets that included the C61 gene but did not include the RPP30 gene).

Population 3, with the higher of two intermediate FAM intensities, corresponds to droplets that are positive to RPP30 and negative for C61 (i.e., droplets that included the RPP30 gene but did not include the C61 gene).

Population 4, with the highest FAM intensity, corresponds to droplets that are positive for RPP30 and C61 (i.e., droplets that included both genes).

The number of droplets in each population may be counted using any suitable mechanism(s), during or following data acquisition. Here, because the intensities are widely separated, the number may be counted by assigning suitable intensity ranges or intervals to each population, as in Example 1, so that droplets falling within a selected intensity range are designated as falling within the population corresponding to that range. The results of such counting are summarized in the following table:

|  | RPP30 | C61 | # Droplets |
| --- | --- | --- | --- |
| Population 4 | + | + | 1168 |
| Population 3 | + | − | 2865 |
| Population 2 | − | + | 2854 |
| Population 1 | − | − | 6782 |

Here, + means that the assay is positive for the indicated gene (i.e., that the indicated gene is present), and − means that the assay is negative for the indicated gene (i.e., that the indicated gene was absent). There are 4033 droplets containing RPP30 (i.e., that are positive for RPP30, irrespective of whether they are positive or negative for C61), as determined by adding the number of droplets in Populations 3 and 4 (i.e., by adding 2865 and 1168, respectively). There are 4022 droplets containing C61 (i.e., that are positive for C61, irrespective of whether they are positive or negative for RPP30), as determined by adding the number of droplets in Populations 2 and 4 (i.e., by adding 2854 and 1168, respectively). Thus, the ratio of C61 to RPP30 is 4022/4033=0.997=1:1 within experimental error. Thus, because RPP30 is known to have two copies per genome, C61 must also have two copies (i.e., the copy number of C61 is two). In many cases, concentrations of the targets are determined by Poisson statistics (e.g., using one or more of Equations (2)-(5)), before a ratio of target levels is determined.

FIG. 6 shows FAM intensities for the C61/RPP30 system of FIG. 5 for twelve different sets of droplets exposed to twelve different annealing temperatures (denoted, from left to right, 55.0, 55.2, . . . , 64.6, and 64.9) during thermal cycling to promote target amplification. The data show that there is sufficient resolution between the four populations to perform the assay in a single channel under a variety of experimental conditions. The data shown in FIG. 5 correspond to one of the conditions in this plot, namely, amplification with an annealing temperature of 59.1° C. (marked in FIG. 6 with an arrowhead).

The annealing temperature may be selected from among the various temperatures tested, based on comparison of collected intensity data. For example, the resolution or separation of each population of droplets from one another in the plot for the various annealing temperatures may be compared to permit selection of a suitable annealing temperature for further data collection and/or analysis. For example, here, the annealing temperature of 59.1° C. offers the best separation between each different population of droplets within the set. In particular, at this annealing temperature, data from double-positive droplets (RPP30+/C61+; the population of highest intensity) are well resolved from data for single-positive droplets (RPP30+ or C61+; the two populations of intermediate intensity), which in turn are well resolved from each other and from data for double-negative droplets (RPP30−/C61−; the population of lowest intensity).

The resolution provided by selection of an optimal annealing temperature may permit determination, for each target, a respective number of droplets that are positive for the target alone at the selected annealing temperature. Also, at least one number of droplets positive for more than one target may be determined. The total number of droplets positive for each target then may be determined based on the respective numbers and the at least one number.

In some cases, signal detection may be performed first on only a fraction of each set of droplets. Additional droplets from the particular set corresponding to the selected annealing temperature then may be run through the detector to provide additional data for analysis. In other cases, only a fraction of the data collected for each set of droplets may be plotted and/or compared, and then additional data collected for the particular set corresponding to the selected annealing temperature may be plotted and/or analyzed.

Example 3

Digital PCR Assay to Assess Copy Number of C63

Figure 7:
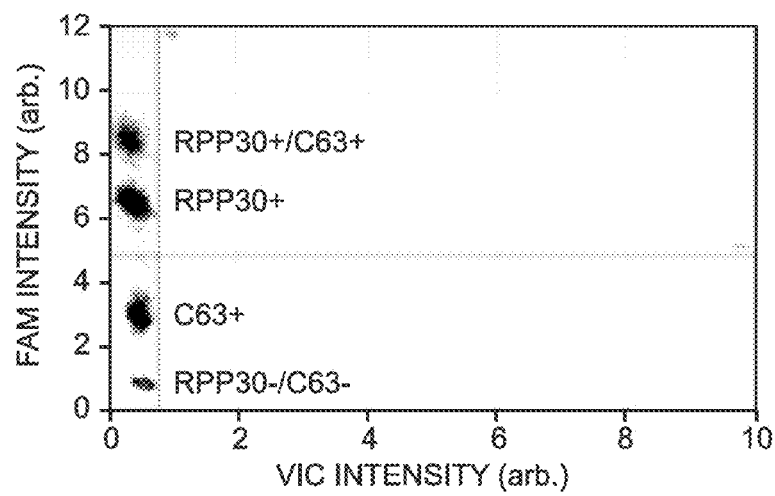
FIG. 7 is an exemplary scatter plot showing droplet (or peak) intensities for a C63/RPP30 droplet assay, where data from reporters for C63 and RPP30 are collected and plotted as a function of intensity in a FAM channel (vertical axis) versus intensity in a VIC channel (horizontal axis) for each detected event (i.e., each droplet).

This example describes a second exemplary digital PCR assay, in which multiplexing in a single channel is used to assess copy number of the C63 gene; see FIGS. 7 and 8. Specifically, signals from two probes, one for the gene of interest, C63, and one for a reference gene, again RPP30, are collected in a single channel and used to assess the number of copies of the gene of interest relative to the number of copies of the reference gene.

FIG. 7 is a graph showing data for the exemplary C63/RPP30 system. Like FIG. 5, FIG. 7 shows intensity in the FAM channel plotted as a function of intensity in the VIC channel for each droplet in a digital PCR assay. However, unlike FIG. 5, this system includes probes for RPP30 and C63 instead of RPP30 and C61. The data again show four distinct populations, corresponding in order of decreasing intensity in the FAM channel to RPP30+/C63+, RPP30+/C63−, RPP30−/C63+, and RPP30−/C63−. The number of droplets counted in each of these bins corresponds to 3552 RPP30 positive droplets, 3441 C63 positive droplets, and 6224 negative droplets. Thus, the ratio of C63 to RPP30 is 3441/3552=0.969=1:1 within experimental error. Thus, like C61, C63 must have two copies (i.e., the copy number of C63 is two).

Figure 8A:
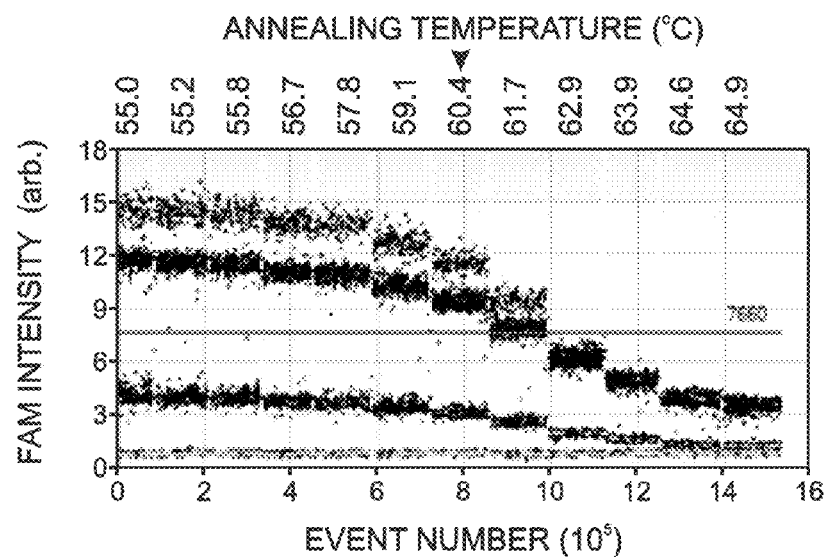
FIG. 8A) and VIC intensities (bottom panel.
Figure 8B:
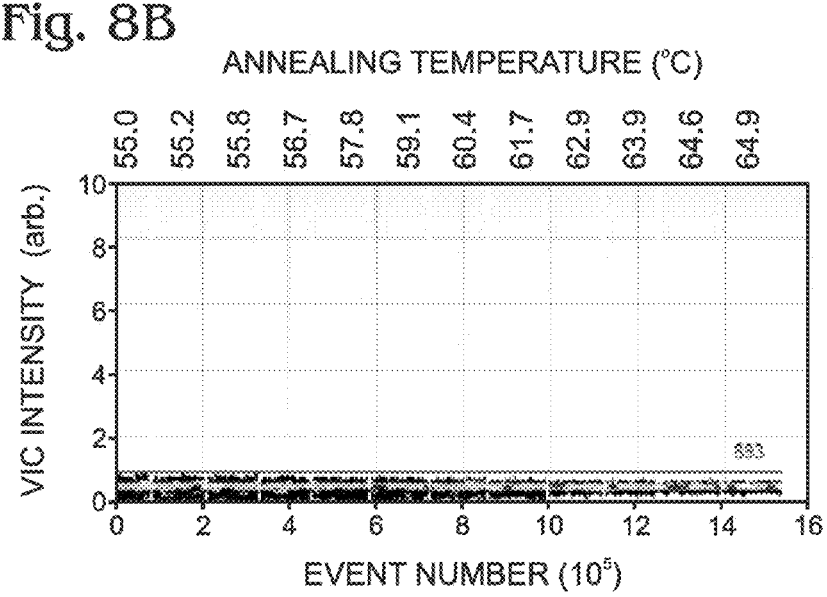
FIG. 8B) for the C63/RPP30 droplet assay of FIG. 7, for twelve different sets of assay conditions, namely, amplification of the C61 and RPP30 targets with different annealing temperatures (given in degrees Celsius and denoted, from left to right, 55.0, 55.2, . . . , 64.6, and 64.9).

FIG. 8A shows FAM intensities and FIG. 8B shows VIC intensities for the C63/RPP30 system of FIG. 7 for twelve different sets of experimental conditions (i.e., different annealing temperatures for amplification). The data show that there is sufficient resolution between the four populations to perform the assay in a single channel under a variety of experimental conditions. The data shown in FIG. 7 correspond to one of the conditions in these plots.

Example 4

Digital Assay with More Luminophores than Optical Channels

Figure 9:
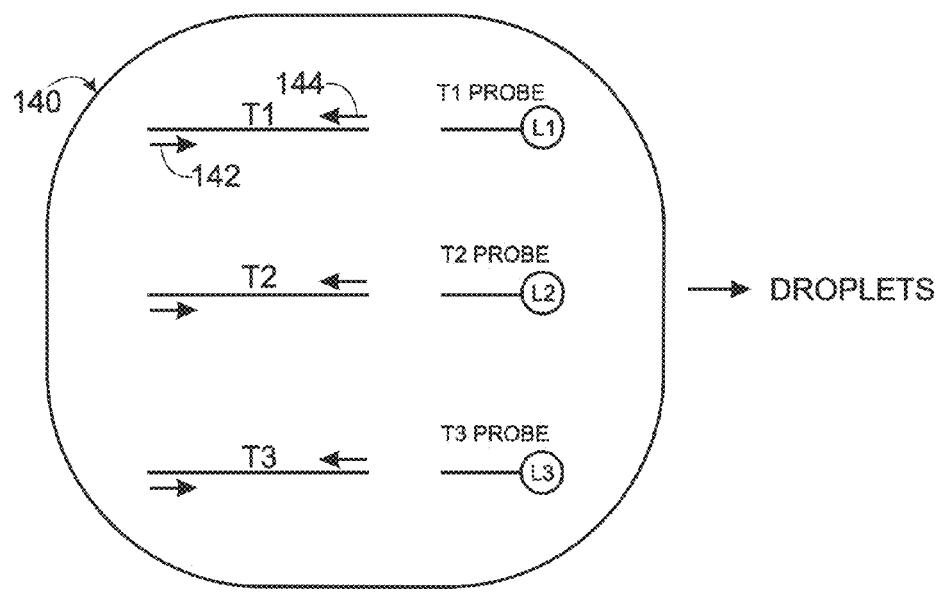
FIG. 9 is a schematic representation of an exemplary bulk phase mixture being separated into droplets during performance of an exemplary multiplexed digital assay for three or more distinct targets (T1, T2, and T3) using a different reporter for detecting amplification of each target (a T1 probe, a T2 probe, and a T3 probe) each including a different luminophore (L1, L2, and L3, respectively), in accordance with aspects of the present disclosure.
Figure 10:
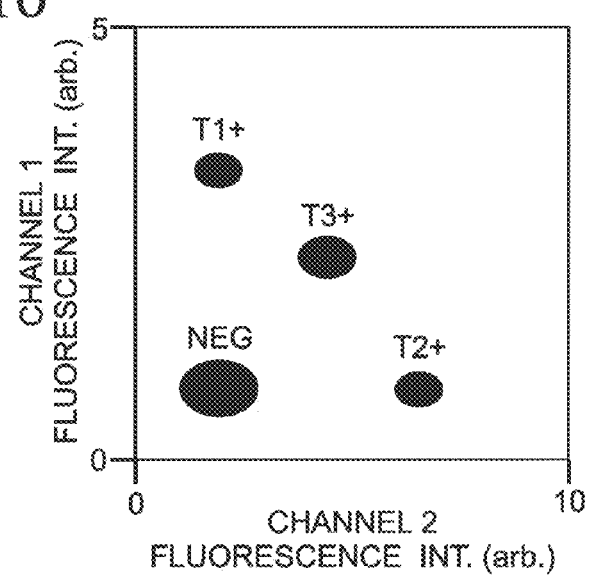
FIG. 10 is a schematic representation of an exemplary scatter plot showing droplet (or peak) intensities for a T1/T2/T3 droplet assay that may be performed with the droplets of FIG. 9, where data from the T1, T2, and T3 probes are collected in a first optical channel and a second optical channel and plotted as a function of intensity in the first channel (vertical axis) versus intensity in the second channel (horizontal axis), with intensities produced by exemplary populations or clusters of negative (NEG), T1-positive (T1+), T2-positive (T2+), and T3-positive (T3+) droplets represented by filled ellipses, in accordance with aspects of the present disclosure.

This example describes an exemplary digital assay with multiplexed analysis of targets using more luminophores than the number of optical channels used for detecting signals from the luminophores; see FIGS. 9 and 10.

FIG. 9 shows an exemplary bulk phase mixture 140 being separated into droplets during performance of an exemplary digital assay with multiplexed detection of three or more distinct targets (e.g., identified here as T1, T2, and T3). Mixture 140 may include a forward primer 142 and a reverse primer 144 for each target. The mixture also may include a reporter for amplification of each target (such as a T1 probe, a T2 probe, and a T3 probe). Each reporter may be a probe including an oligonucleotide labeled with a different luminophore (namely, L1, L2, and L3, respectively). Accordingly, luminescence from the T1-T3 probes, and more particularly, the L1, L2, and L3 luminophores, may report whether or not targets T1, T2, and T3, respectively, are present in each individual droplet. Each probe also may include a quencher for the associated luminophore.

FIG. 10 schematically represents an exemplary scatter plot showing droplet (or peak) intensities for a T1/T2/T3 droplet assay that may be performed with the droplets of FIG. 9. Data from the T1, T2, and T3 probes are collected in a first optical channel and a second optical channel and plotted as a function of intensity in the first channel (vertical axis) versus intensity in second channel (horizontal axis). Intensities produced by exemplary populations or clusters of negative, T1-positive, T2-positive, and T3-positive droplets are identified by filled ellipses, with the size of each ellipse corresponding to the number of droplets in each population. To simplify the presentation, double-positive populations (T1+/T2+, T1+/T3+, and T2+/T3+) and the triple-positive population (T1+/T2+/T3+) are not shown. (However, see Example 7 for an exemplary distribution of single- and multiple-positive droplets.)

Each luminophore may be at least predominantly or substantially exclusively detectable in only one optical channel, or may be substantially detectable in two or more optical channels. For example, L1 of the T1 probe is substantially detectable in the first channel but not the second channel, L2 of the T2 probe is substantially detectable in the second channel but not the first channel, and L3 of the T3 probe is substantially detectable in both channels. More generally, L3 may generate a distinguishable intensity and/or a different ratio of signal intensities for amplification of the T3 target in each channel relative to the intensity and/or ratio produced by L1 for amplification of the T1 target and produced by L2 for amplification of the T2 target. As a result, the population of T3-only positives is resolved from the T1-only and T2-only populations. Also, the populations containing more than one target may be resolved and distinguishable from one another and from the single-target populations and the negative population (e.g., see Example 7).

Any suitable number of targets may be analyzed with the approach presented in this Example. For example, R targets may be analyzed using R distinct luminophores and less than R optical channels for detection of target amplification.

Example 5

Adjustment of Individual Assay Concentrations in a Multiplexed Assay

Figure 11:
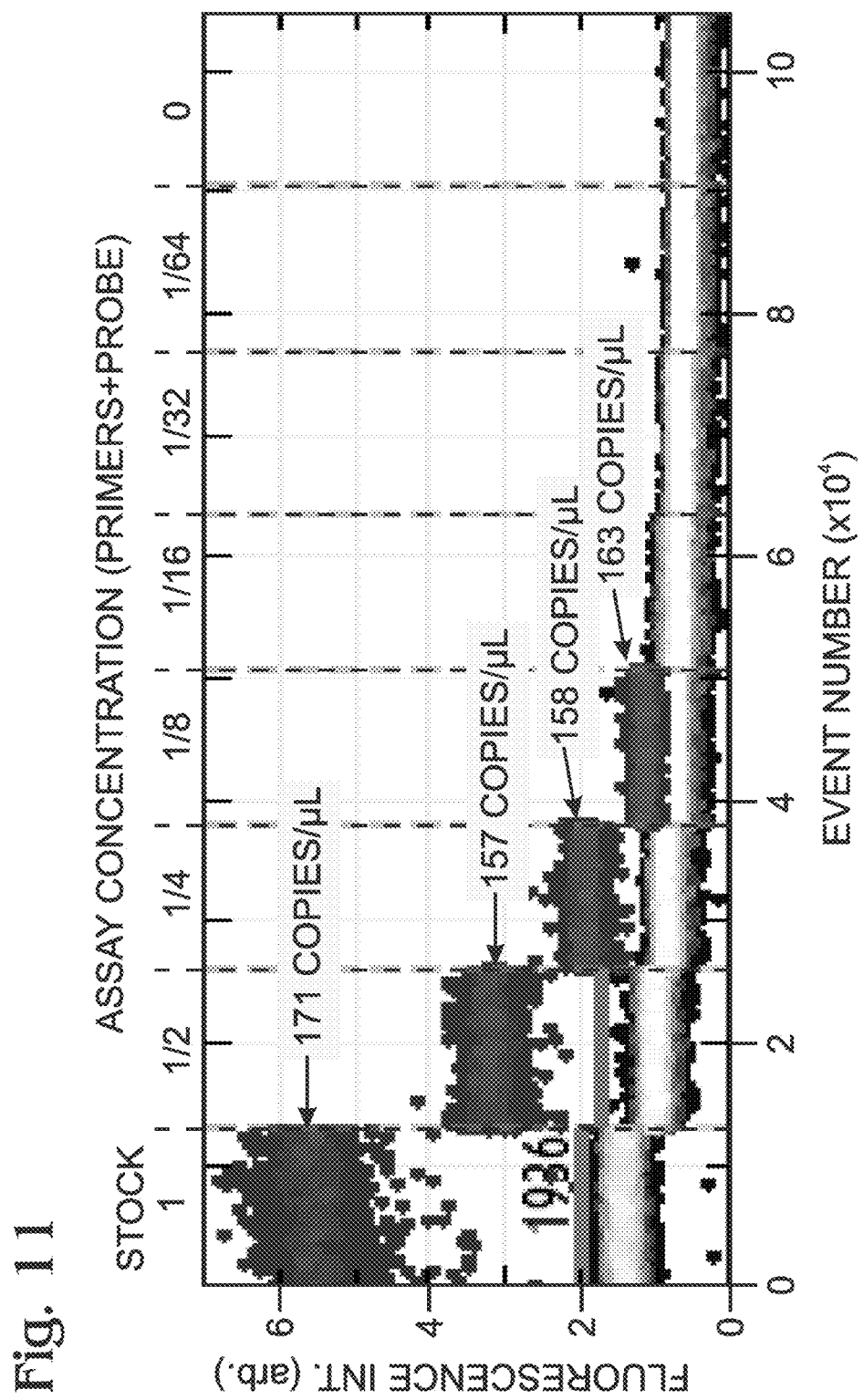
FIG. 11 is a graph of fluorescence intensity data collected in a one-target amplification assay performed in droplets, at the indicated assay concentration for primers and probe, to illustrate how the assay concentration can be modified to increase or decrease the level of the intensity signal for each amplification-positive (and/or negative) droplet (or "event"), in accordance with aspects of the present disclosure.

This example describes an exemplary approach for adjusting the endpoint intensity of individual target assays of a multiplexed assay; see FIG. 11.

Digital PCR enables accurate, precise, and sensitive quantification of specific nucleic acid sequences. In addition to the detection of two targets using two different fluorophores and two optical channels for collecting data from the fluorophores, it is possible to increase the number of targets detected by varying parameters that affect PCR efficiency and thus the level of endpoint fluorescence for each target. The present disclosure describes a method to multiplex assays by adjusting the endpoint fluorescence level (and/or spectrum) for each target assay (e.g., by changing the concentration of primers and/or probes and/or the type of fluorophores used). This approach allows users to expand the number of simultaneously detected targets without increasing the number of optical channels for detection.

Increasing the number of potential targets per test is a significant improvement for digital PCR, augmenting dramatically the information output of each sample.

FIG. 11 shows a graph of fluorescence intensity data obtained in a one-target amplification assay performed in droplets. Here, fluorescence is measured with a single detector (one optical channel) as droplets flow past the detector in a stream of carrier fluid. Droplets or "events" may be identified as periodic spikes or waves in the fluorescence signal (e.g., see FIG. 4 above). Each droplet/event then may be assigned at least one fluorescence value, e.g., representing an amplitude and/or integrated intensity, among others, of the corresponding signal wave. The fluorescence intensity value (in arbitrary units ("arb.")) for each droplet then may be plotted as a function of event number. At the left side of the graph ("stock"), droplets that are amplification-negative and amplification-positive form well-resolved bands of lower and higher intensity, respectively.

The assay was performed with a series of two-fold dilutions of assay reagents, namely, the primers and the probe, as indicated above the graph. Changing the concentration of one or more assay reagents, other than the template, may be described as changing the assay concentration. Each successive dilution of the assay (primers and probe), up to eight-fold, markedly decreased the level (interchangeably termed amplitude) of the fluorescence endpoint for the target-positive droplets (indicated by arrows), and more subtly decreased the intensity of the target-negative droplets. However, droplet counts from each successive dilution up to eight-fold provided a reproducible target concentration (presented as "copies/µL"). Therefore, changing the fluorescence endpoint for a target can be achieved without degrading the ability to accurately and reliably determine the target concentration. The probe and primers for an assay each may be adjusted by the same factor, as shown in FIG. 11, or each may be adjusted by a different factor (or not at all).

The present disclosure provides a method to assay for multiple targets (multiplex) through digital PCR, by varying the assay used for each target. An assay may include a set of primers (forward and reverse) and a fluorescently labeled probe. In digital PCR, droplets may be segregated by the levels of fluorescence produced by the PCR reaction. The level of fluorescence for a droplet is dependent on a multitude of factors (reaction efficiency, type of fluorophores, amplicon size, etc.). By changing the concentration of an assay, the reaction efficiency of a particular target can be affected, which may result in a difference in fluorescence level that allows populations detected with the same fluorophore to be distinguished from one another. By changing the assay concentrations of two different fluorophores, additional targets may be detected in the same multiplexed reaction. In some cases, fluorescence intensity may be adjusted by varying the concentration of one or both primers for a target. Varying primer concentration without changing the probe concentration may be useful in assays where the same probe is used to detect two targets, but each of the two targets is amplified with at least one different primer. In some cases, the level of the fluorescence for a target may be adjusted by changing the annealing temperature used for thermocycling, the total concentration of dNTPs, the amounts of individual dNTPs relative to each other (e.g., if the two targets have substantially different base compositions), or the like.

Example 6

Multiplexed Assays with Orthogonal Droplet Populations

This example describes exemplary multiplexed digital assays performed on R targets, where R is at least three, and with fewer than R optical channels, where amplification of each target is substantially detectable in only one of the optical channels (e.g., two optical channels). As a result, droplet populations positive for different combinations of the targets are arranged in rows and columns in a plot of detected amplification data; see FIGS. 12-18.

Figure 12:
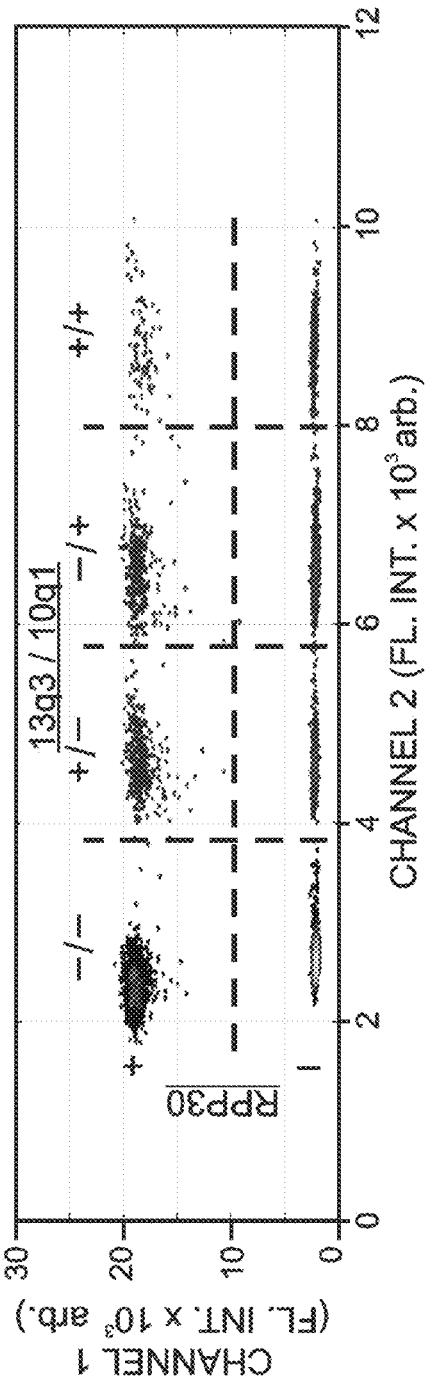
FIG. 12 is a 2-D scatter plot of fluorescence intensity ("FL. INT.") data obtained from individual droplets detected in two optical channels during performance of a triplex amplification assay for three targets (RPP30, Chr13q3, and Chr10q1), with the sample (template DNA) digested before amplification with a restriction enzyme (AluI) that does not cut within any of the templates for the targets, and with the target composition of each droplet population indicated ("−" is negative and "+" is positive for each indicated target), in accordance with aspects of the present disclosure.

FIG. 12 is a 2-D scatter plot of fluorescence intensity data obtained from individual droplets detected in two optical channels during performance of a triplex amplification assay for three targets (RPP30, Chr10q1, and Chr13q3). Each dot represents a single droplet. Before droplet formation, the template DNA was digested with AluI, which reduces the size of the template DNA but does not cut between the priming sites for any of the three targets. Amplification of RPP30 was detected with a FAM-labeled probe in optical channel one, and amplification of chromosome 10 and chromosome 13 regions (10q1 and 13q3) was detected with VIC-labeled probes in optical channel two, at a different waveband of light emission than channel one. The three assays (RPP30, Chr10q1, and Chr13q3) were respectively run at probe/primer concentrations of 1×, 1×, and 0.6×. Accordingly, the chromosome 13q3 assay produced a lower fluorescence endpoint signal than the chromosome 10q1 assay because the 13q3 assay was more dilute (0.6× versus 1×).

Eight droplet populations are visible and resolved from each other in FIG. 12, with the droplet populations separated from one another by dashed lines. The populations are as follows: one triple negative ("empty"), three single positives (each positive for RPP30, 10q1, or 13q3), three double positives (positive for each pair-wise combination of the targets), and one triple positive (positive for all three targets). The concentrations of the targets can be calculated based on combination of counts from the populations. For example, the concentration of 10q1 can be calculated using Equation (4) and a positive droplet count ($N_+$) representing a combination of the four 10q1-positive populations (and excluding the four 10q1-negative populations), or with Equation (5) using a negative droplet count ($N_-$) representing a combination of only the four 10q1-negative populations (and excluding the four 10q1-positive populations). In any event, counts from a plurality of 10q1-positive populations (e.g., one-half of all populations identified) are excluded.

Figure 13:
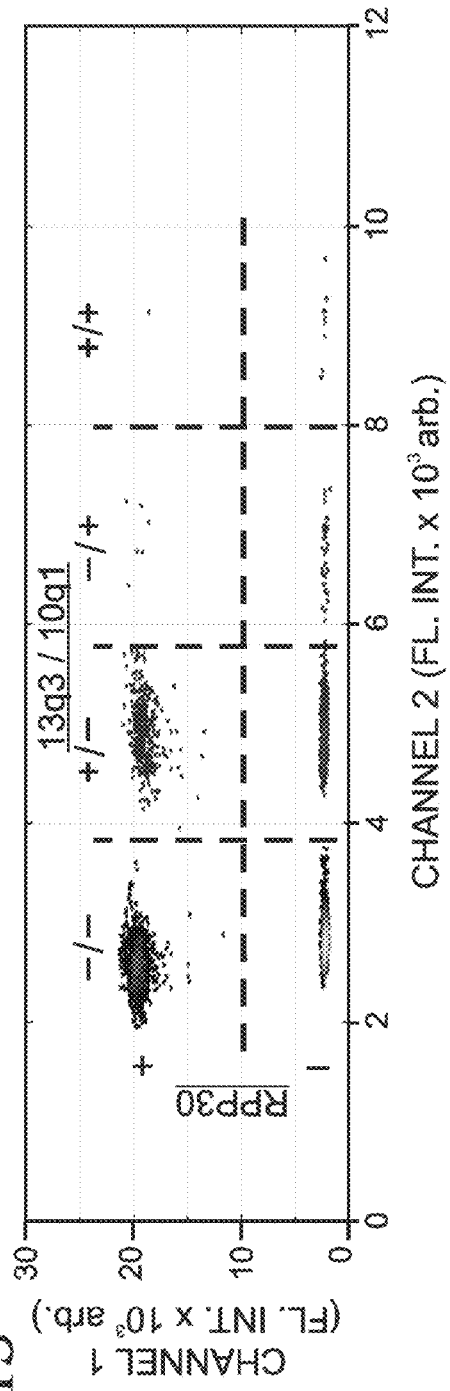
FIG. 13 is another 2-D scatter plot of fluorescence intensity data obtained generally as in FIG. 12 but with the sample (template DNA) digested, before amplification, with a restriction enzyme (HaeIII) that cuts between the priming sites of the Chr10q1 template, in accordance with aspects of the present disclosure.

FIG. 13 shows another 2-D scatter plot of fluorescence intensity data obtained generally as in FIG. 12 but with the sample (template DNA) digested before amplification with a restriction enzyme (HaeIII) that cuts between the priming sites of the Chr10q1 template. As a result, the droplet counts for each of the four 10q1-positive populations decreases dramatically, while the droplet counts for each of the four 10q1-negative populations increases, thereby providing validation for the assignment of droplet populations. Also, the experiment demonstrates that the multiplexed assay system can produce an additive effect of the fluorescence levels from two different assays using the same fluorophore for both probes.

Figure 14:
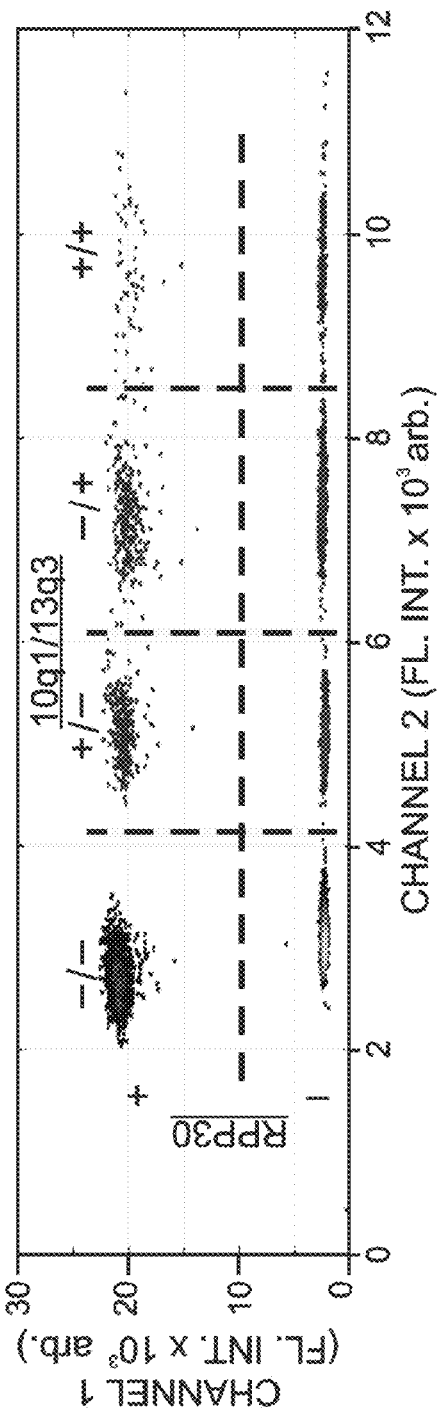
FIG. 14 is a 2-D scatter plot of fluorescence intensity data obtained from individual droplets detected in two optical channels during performance of a triplex amplification assay as in FIG. 12, but with the concentrations of the Chr13q3 and Chr10q1 assays adjusted to changes the endpoint fluorescence level for assay of these targets, such that the relative positions of the corresponding single-positive populations are inverted in the plot, in accordance with aspects of the present disclosure.

FIG. 14 shows a 2-D scatter plot of fluorescence intensity data obtained as in FIG. 12, but with the concentrations of the Chr13q3 and Chr10q1 assays adjusted to change the endpoint fluorescence level for assay of these targets. In particular, the 10q1 assay is performed at a 0.6× concentration (instead of 1×) and the 13q3 assay at a 1× concentration (instead of 0.6×). Accordingly, the positions of droplet populations are rearranged with respect to FIG. 12, with the 10q1-positive populations that are negative for 13q3 having a lower intensity than the 13q3-positive populations that negative for 10q1. As in FIG. 12, the concentration of all three targets is equivalent (i.e., the sample is from a euploid genome).

Figure 15:
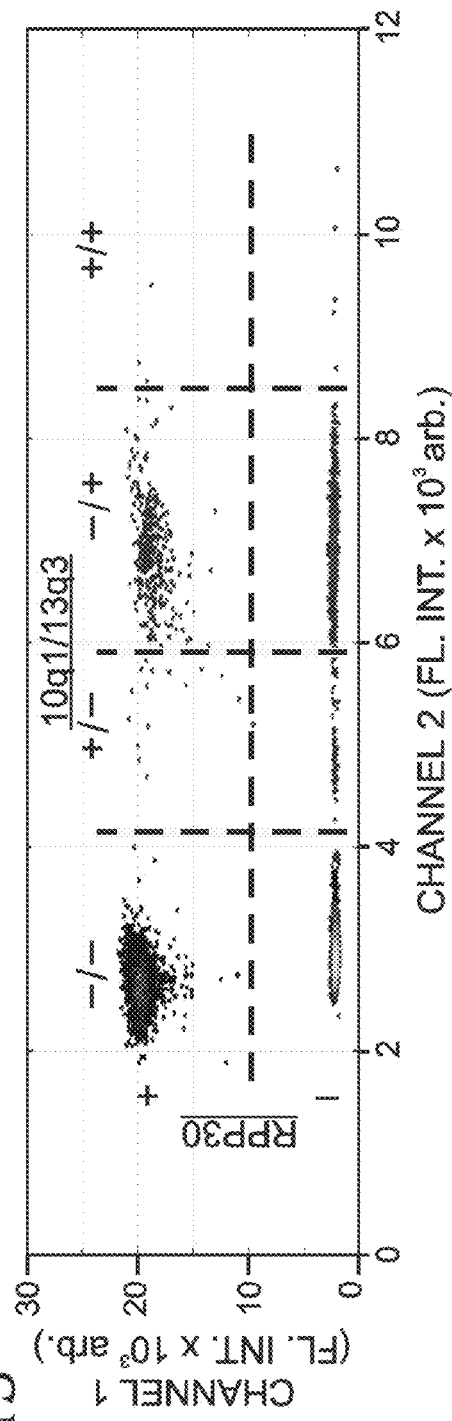
FIG. 15 is another 2-D scatter plot of fluorescence intensity data obtained with the assay concentrations of FIG. 14, but with the sample (template DNA) digested, before ampli- fication, with a restriction enzyme (HaeIII) that cuts between the priming sites of the Chr10q1 template, in accordance with aspects of the present disclosure.

FIG. 15 shows another 2-D scatter plot of fluorescence intensity data obtained with the assay concentrations of FIG. 14, but with the sample (template DNA) digested before amplification with a restriction enzyme (HaeIII) that cuts between the priming sites of the Chr10q1 template. The digestion produces a significant reduction of populations containing Chr10q1-positive droplets, therefore validating the detection pattern.

Figure 16:
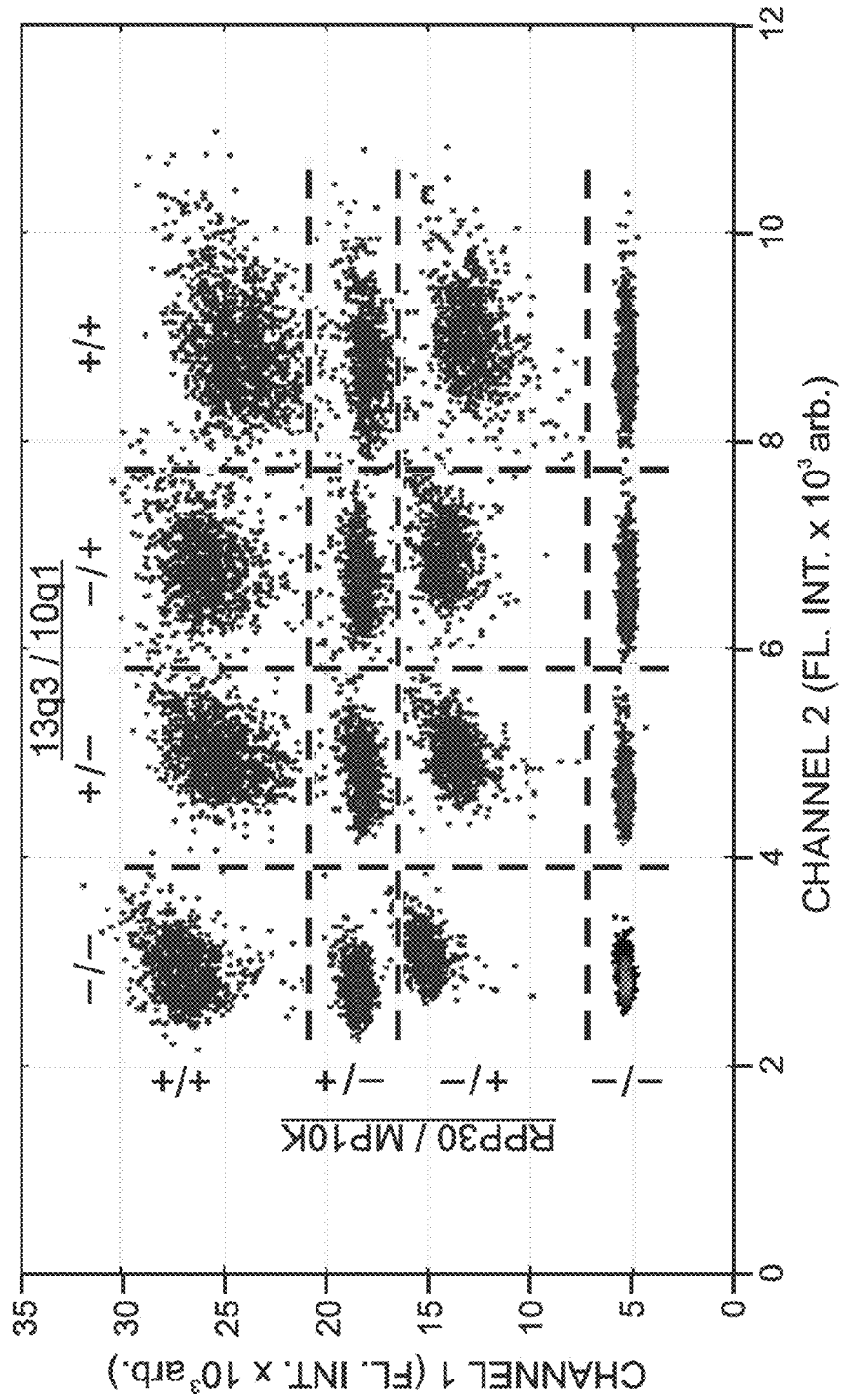
FIG. 16 is a 2-D scatter plot of fluorescence intensity data obtained from individual droplets detected in two optical channels during performance of a tetraplex amplification assay for four targets (RPP30, MP10K, Chr13q3, and Chr10q1), with the sample (template DNA) digested before amplification with a restriction enzyme (AluI) that does not cut within any of the templates for the targets, and with the resulting droplet populations separated by dashed lines and the target composition of each droplet population indicated ("−" is negative and "+" is positive for each indicated target), in accordance with aspects of the present disclosure.

FIG. 16 shows a 2-D scatter plot of fluorescence intensity data obtained from individual droplets detected in two optical channels during performance of a tetraplex amplification assay for four targets (RPP30, MP10K, Chr13q3, and Chr10q1). RPP30 and MP10K targets were detected with FAM-labeled probes using 1× and 1.5× assay concentrations, respectively. Chr13q3 and Chr10q1 targets were detected with VIC-labeled probes using 0.6× and 1× assay concentrations, respectively. The resulting droplet populations are separated by dashed lines in the plot, and the target composition of each droplet population is indicated ("−" is negative and "+" is positive for each indicated target). The assay provides simultaneous detection of four different targets in two optical channels. The results illustrate the capacity of the multiplexed assay system to separate discrete populations by levels of fluorescence using the same fluorophores.

The droplet populations have an orthogonal arrangement in a scatter plot with a linear scale for each axis. Stated differently, the droplet populations may form a matrix or rectangular array, which may have $2^R$ populations, where R is the number of targets. The populations may form an array having a plurality of rows and a plurality of columns each containing two or more populations. Each row may contain the same number of populations, and each column may contain the same number of populations. In some embodiments, each of the single-positive populations may be restricted to an edge of the array, such as the left-most column or the bottom row of the array. With this arrangement, multiply-positive populations can be distributed in the optical space above the bottom row and to the right of the left-most column, without overlapping one another or any single-positive populations. Also, the positions of all of the multiply-positive populations can be predicted from the positions of the single-positive populations, simplifying the task of selecting suitable intensities for each single-positive population during assay development and optimization. To achieve this arrangement of single-positive populations, each target may have a corresponding probe that is detectable substantially exclusively in only one of the optical channels, such that amplification of each target is detected substantially in only one of the optical channels. For example, amplification of RPP30 and MP10K (FAM-labeled probes) is detectable substantially exclusively in channel one, and amplification of 13q3 and 10q1 (VIC-labeled probes) substantially exclusively in channel two.

Figure 17:
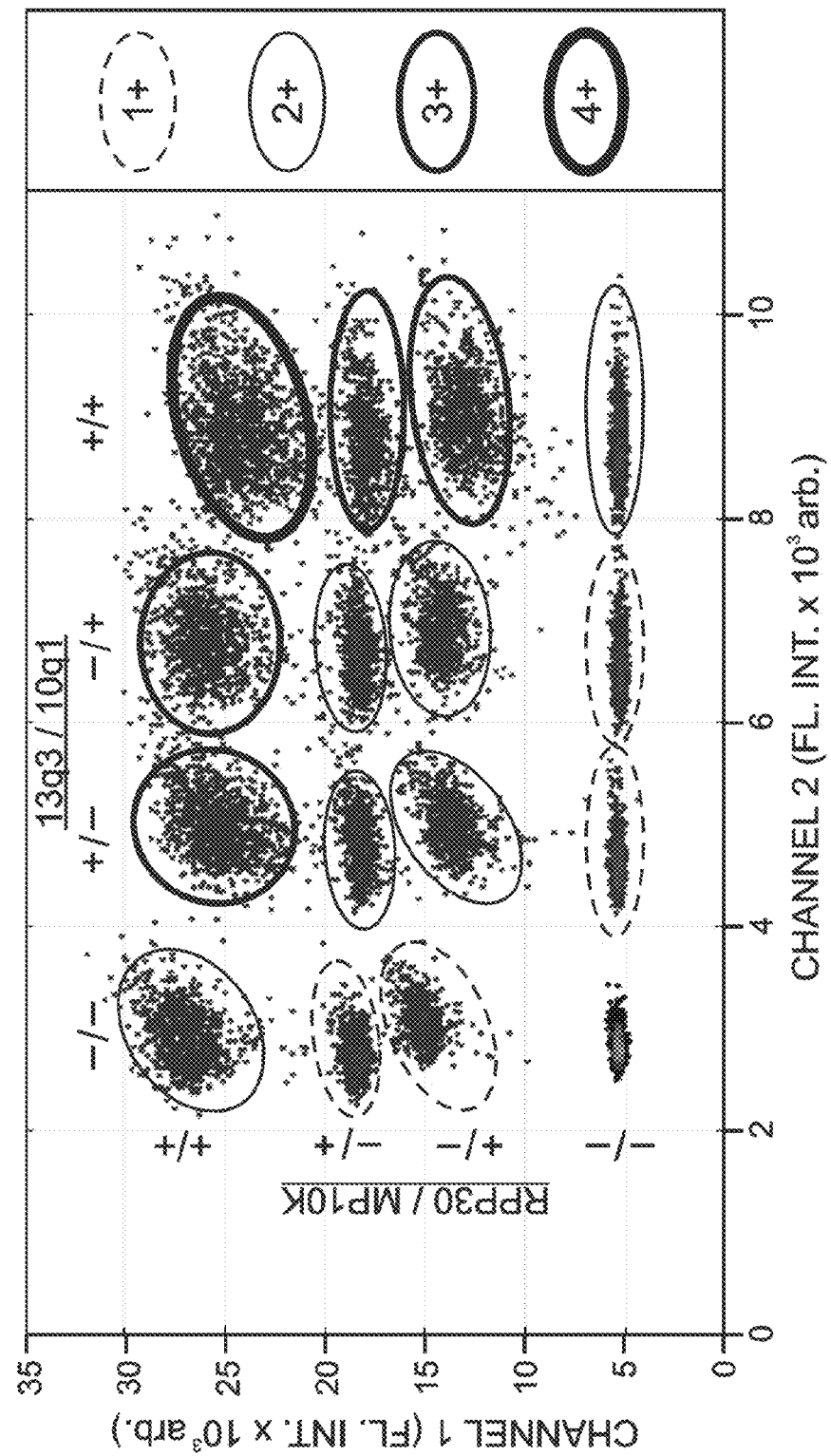
FIG. 17 is the 2-D scatter plot of FIG. 16, with the dashed lines removed and each droplet population circled using a line weight that indicates the number of different targets for which each population is amplification positive, in accordance with aspects of the present disclosure.

FIG. 17 shows the 2-D scatter plot of FIG. 16, with the dashed lines removed and each droplet population circled using a line weight that indicates the number of different targets for which each population is amplification positive. The plot has one quadruple-negative population (at the bottom left corner of the population array), four single-positive populations ("1+"), six double-positive populations ("2+"), four triple-positive populations (3+"), and one quadruple-positive population ("4+").

Figure 18:
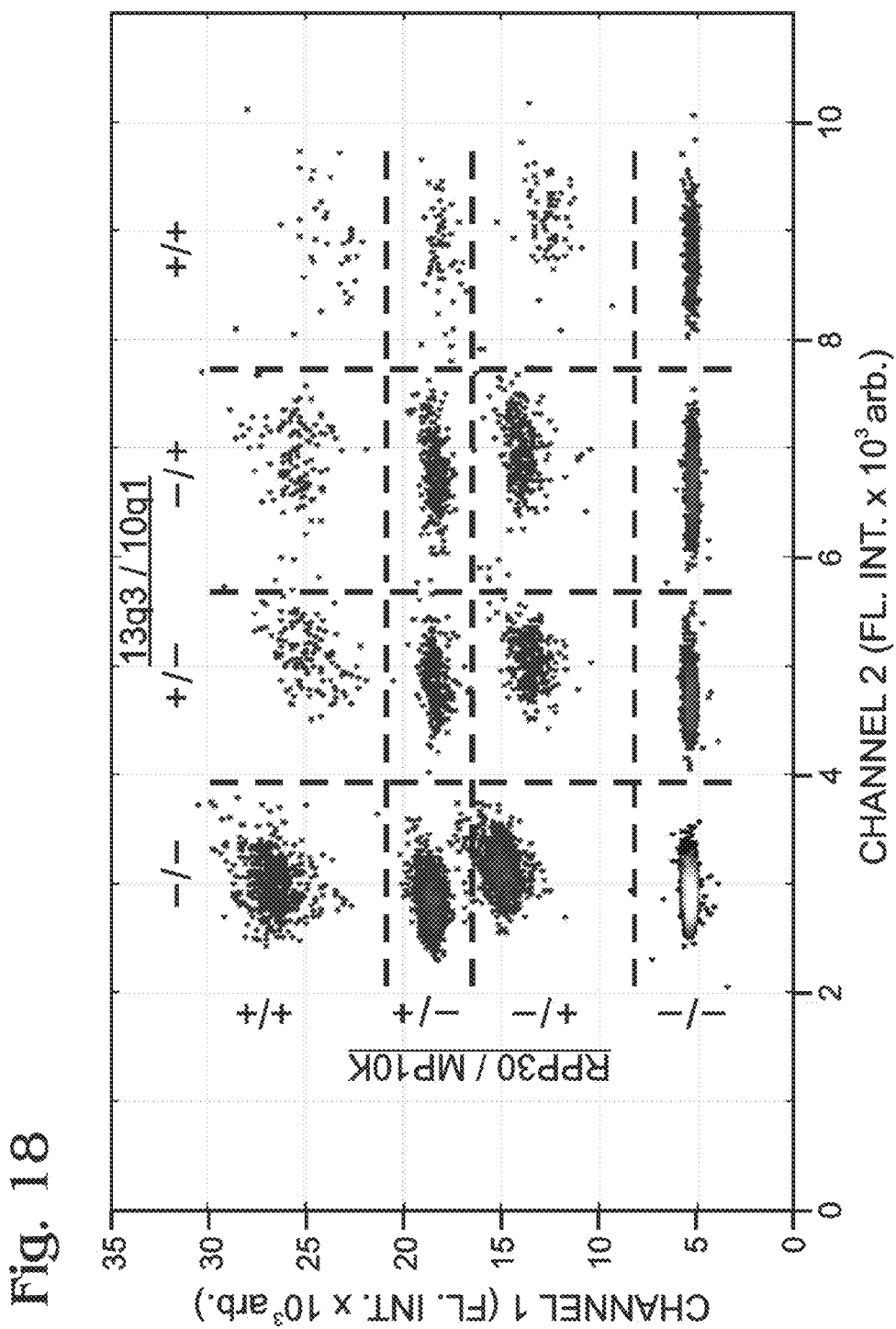
FIG. 18 is a 2-D scatter plot of fluorescence intensity data obtained with the tetraplex assay of FIG. 16, but with the sample (template DNA) diluted by a factor of four relative to FIG. 16, in accordance with aspects of the present disclosure.

FIG. 18 shows a 2-D scatter plot of fluorescence intensity data obtained with the tetraplex assay of FIG. 16, but with the sample (template DNA) diluted by a factor of four relative to FIG. 16. The plot exhibits a visible reduction of droplets from positive populations, particularly the triple- and quadruple-positive populations. The plot demonstrates that the multiplexed assay system retains its ability to quantify targets in a multiplex setting.

Example 7

Multiplexed Assays with Non-orthogonal Droplet Populations

This example describes exemplary multiplexed digital assays performed on R targets, where R is at least three, and with fewer than R optical channels (e.g., only two optical channels), where amplification of at least one, two or more, or each of the targets is substantially detectable in two or more of the optical channels. As a result, droplet populations positive for a plurality of combinations of the targets are arranged non-rectangularly, with less apparent order, in a plot of detected amplification data; see FIGS. 19-25.

Figure 19:
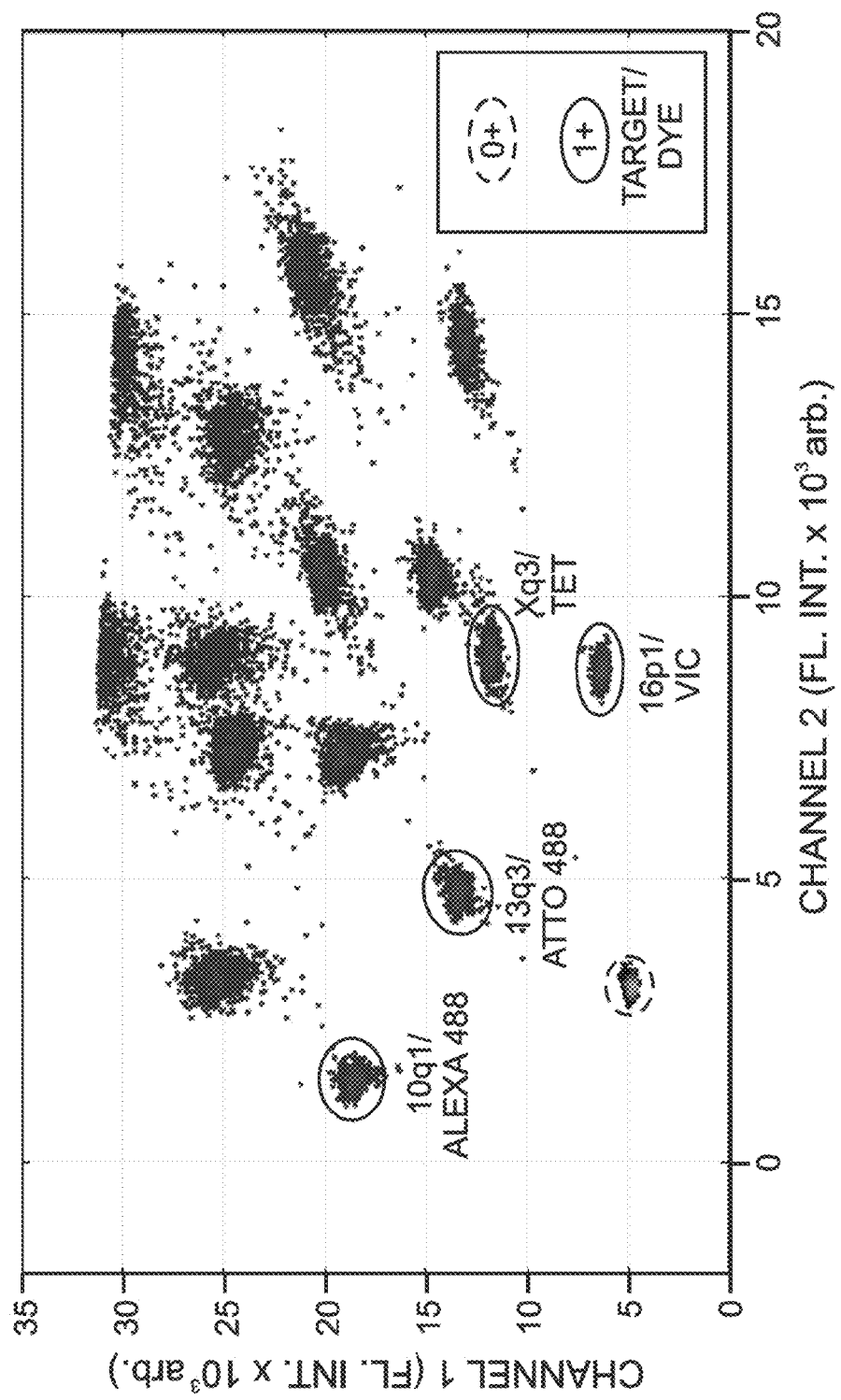
FIG. 19 is a 2-D scatter plot of fluorescence intensity data obtained from individual droplets detected in two optical channels during performance of a tetraplex amplification assay for four targets (Chr10q1, Chr13q3, Chr16 μl, and ChrXq3) using four corresponding probes each containing a different fluorophore (Alexa Fluor® 488 dye, Atto® 488 dye, VIC dye, and TET dye, respectively), with each single-positive population of droplets labeled, in accordance with aspects of the present disclosure.
Figure 21:
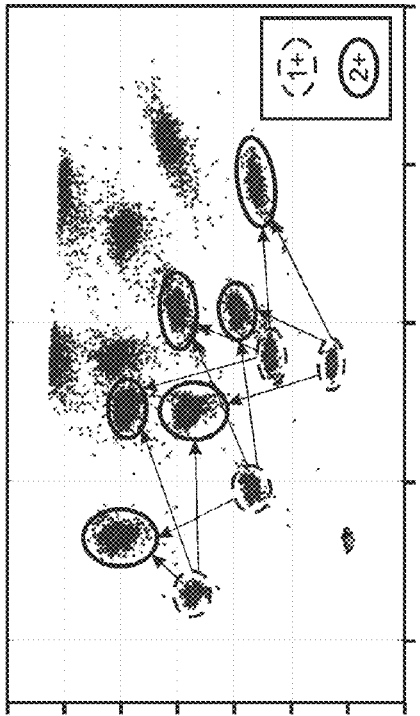
FIGS. 20-23 each reproduce the scatter plot of FIG. 19 and respectively show single-, double-, triple-, and quadruple-positive droplet populations as circled, with arrows indicating the distinct target composition of each population, in accordance with aspects of the present disclosure.
Figure 23:
Figure 20:
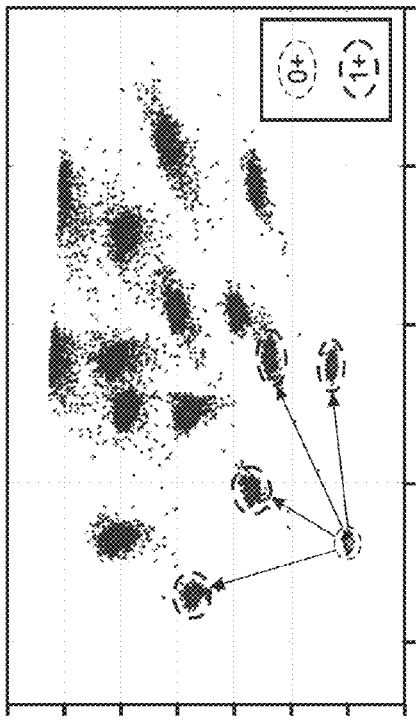
Figure 22:
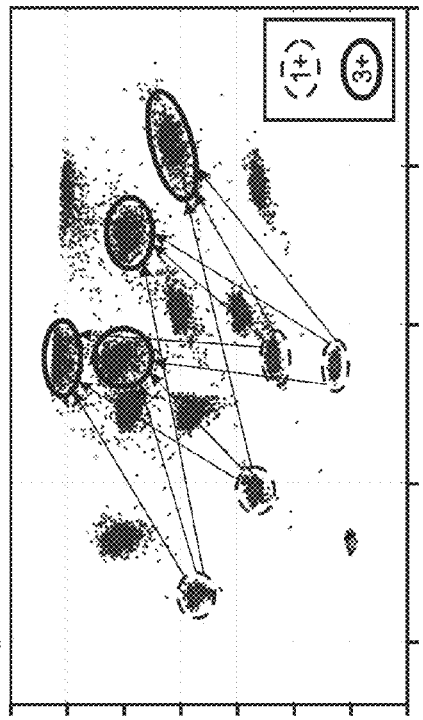

FIG. 19 shows a 2-D scatter plot of fluorescence intensity data obtained from individual droplets detected in two optical channels during performance of a tetraplex amplification assay for four targets (Chr10q1, Chr13q3, Chr16p1, and ChrXq3). Each dot represents a single droplet. Amplification of the four targets was detected using four corresponding probes each containing a different fluorophore (Alexa® 488 dye, Atto® 488 dye, VIC dye, and TET dye, respectively), as labeled in the plot. Each resolved dot represents a single droplet. In this experiment, multiplexing was achieved by using "non-traditional" fluorophores (i.e., other than FAM and VIC/HEX), although traditional and non-traditional fluorophores may be used together in a multiplexed assay. Each fluorophore may be attached to a distinct oligonucleotide. Each fluorophore may (or may not) exhibit substantial emission in each optical channel or may be substantially detectable in only one of the optical channels. In the present example, the four fluorophores have distinct spectral profiles, with each detectably emitting light in both optical channels. As a consequence, the droplet populations are arranged in a non-orthogonal pattern that allows differentiation of more targets than the number of optical channels.

FIGS. 20-23 each reproduce the scatter plot of FIG. 19 and respectively show a circle around each single- ("1+"), double- ("2+"), triple- ("3+"), and quadruple ("4+")-droplet population. Arrows indicate the distinct target composition of each population. The assignment of droplet populations was confirmed by performing four different triplex reactions in which each of the different assays (for each target) was separately omitted from the reaction mixture.

Figure 24:
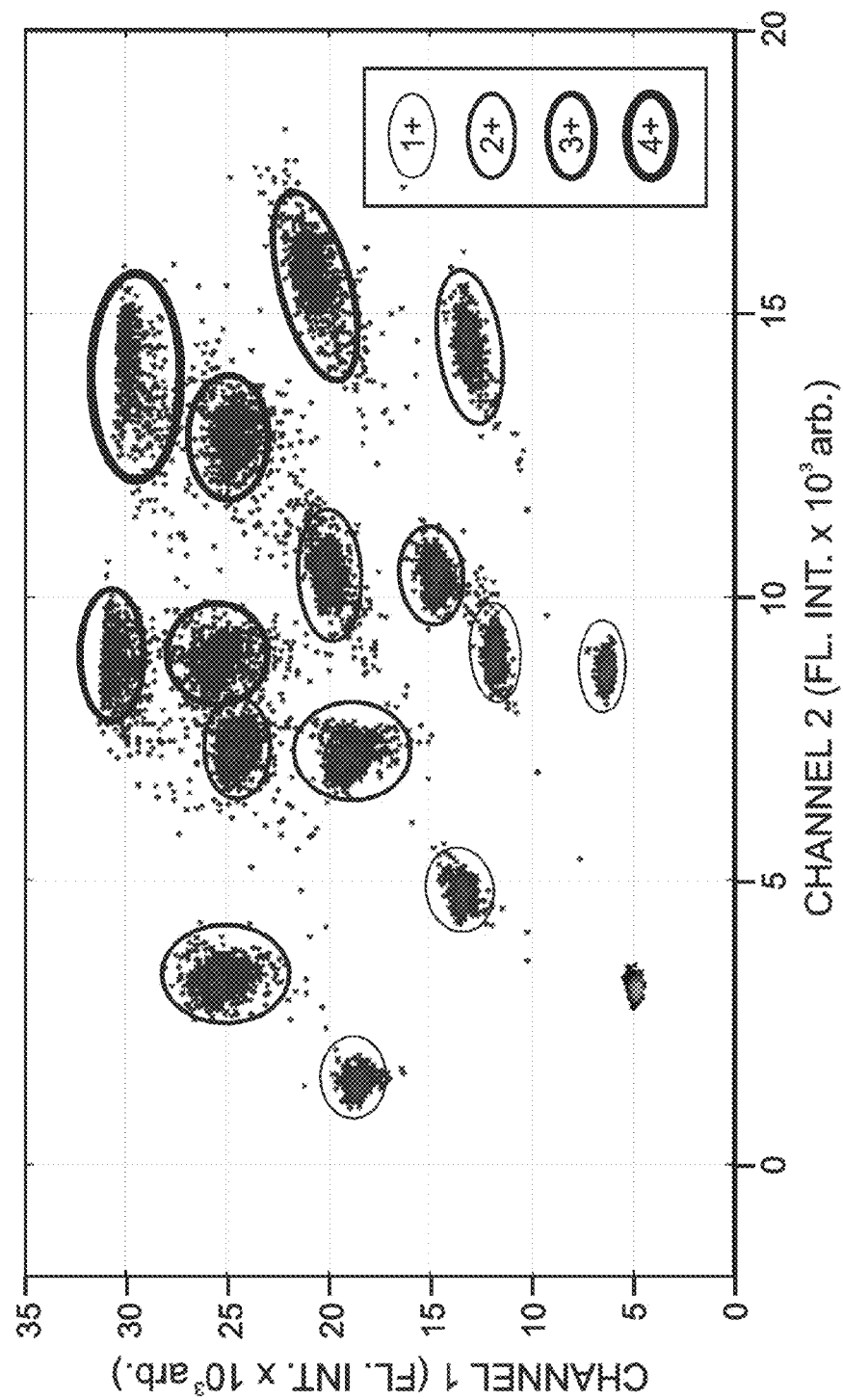
FIG. 24 is a composite of FIGS. 20-23 that marks all of the target-positive droplet populations in the same plot, in accordance with aspects of the present disclosure.

FIG. 24 shows a composite of FIGS. 20-23 that marks all of the droplet populations in the same plot. The approach allows simultaneous identification of all droplet populations.

Figure 25:
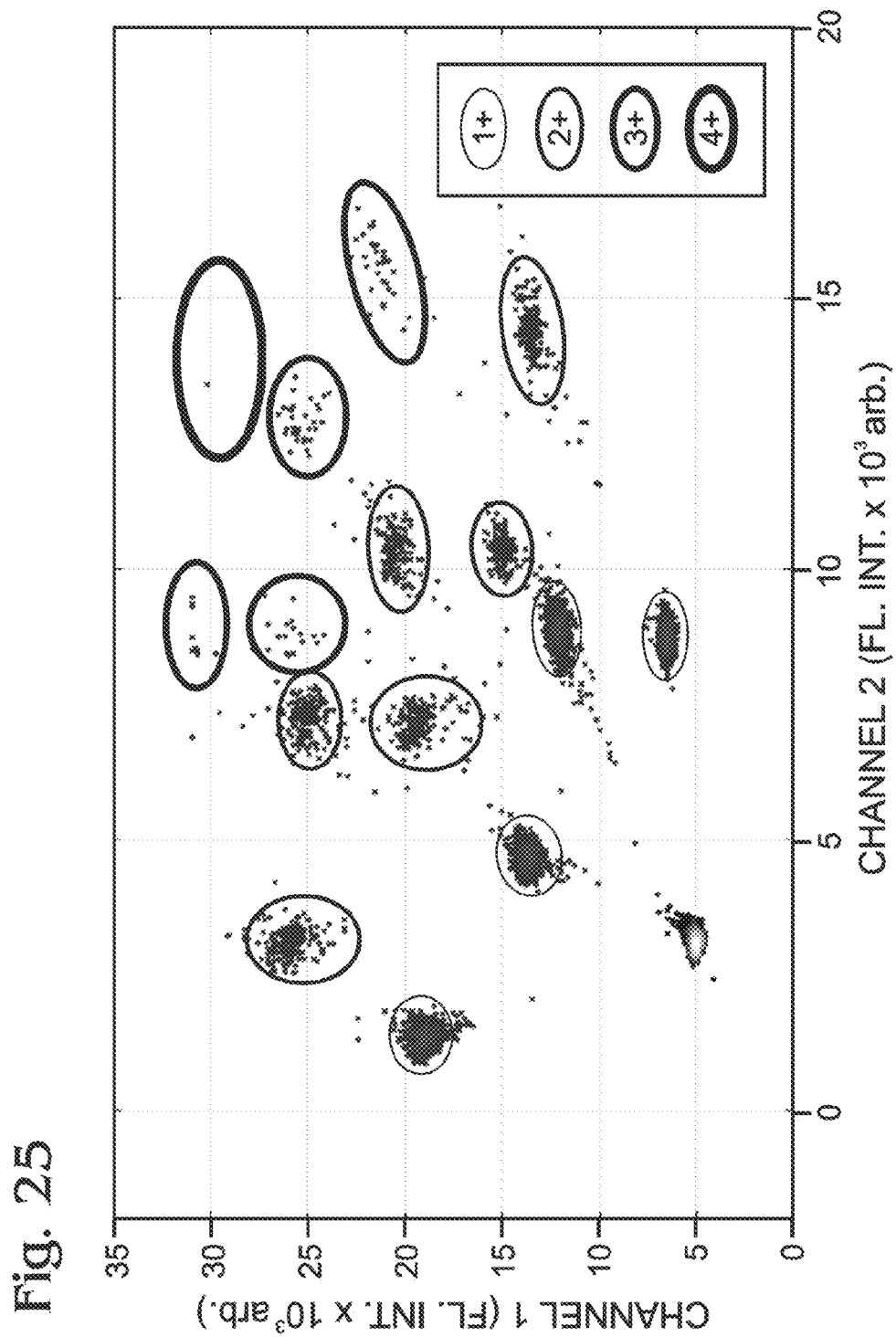
FIG. 25 is a 2-D scatter plot obtained as in FIGS. 19 and 24 but with only one-sixth as much template DNA, in accordance with aspects of the present disclosure.

FIG. 25 is a 2-D scatter plot obtained as in FIGS. 19 and 24 but with only one-sixth the amount of template DNA. The size of each positive population is reduced, with a substantially greater effect on the size of the triple- and- quadruple positive populations. The result illustrates that the multiplexed assay system retains its ability to quantify targets when using combinations of non-traditional fluorophores.

The multiplexed approaches disclosed here permit quantification of more targets that the number of optical channels. Examples 6 and 7 utilize only two optical channels. However, the multiplexed assay system of the present disclosure may collect data in any suitable number of C optical channels, to collect data in a C-dimensional optical space. The data may be processed in a manner analogous to that described above for a two-dimensional optical space.

Example 8

Selected Embodiments

This example describes selected embodiments of exemplary multiplexed digital assays, presented as a series of numbered paragraphs.

1. A method of performing a multiplexed digital assay, comprising: (A) forming droplets that collectively contain R targets; (B) amplifying the targets in the droplets; (C) collecting data representing amplification of the targets in the droplets, the data being collected in fewer than R optical channels; and (D) determining a level of each target with the data, wherein the level determined for at least one of the targets is based in part on a droplet count for a droplet population identified as positive for two of the targets.

2. The method of paragraph 1, wherein R is at least three.

3. The method of paragraph 1 or 2, wherein the data is collected in only two optical channels.

4. The method of paragraph 1, wherein each optical channel represents a different waveband of emitted light.

5. The method of any preceding paragraph, wherein each optical channel represents a different waveband of excitation light.

6. The method of paragraph 1, wherein a different plurality of the droplets contains a copy of each pair of the targets.

7. The method of paragraph 1, wherein at least about 5%, 10%, 20%, or 50% of the droplets contain a pair of the targets.

8. The method of paragraph 1, further comprising a step of identifying from the data a plurality of droplet populations each positive for a different combination of the targets.

9. The method of paragraph 8, wherein forming, amplifying, and collecting are performed such that each droplet population that is positive for exactly two of the targets is at least substantially resolved from each droplet population that is positive for only one of the targets.

10. The method of paragraph 1, further comprising a step of plotting the data such that droplet populations containing different combinations of the targets form a rectangular array.

11. The method of paragraph 10, wherein the array is composed of a plurality of rows and columns, with each row and each column including at least two of the droplet populations.

12. The method of paragraph 10, wherein the step of plotting is performed with respect to a pair of orthogonal axes, and wherein each droplet population that is positive for only one of the targets is arranged along a line that is at least generally parallel to one of the axes.

13. A method of performing a multiplexed digital assay, comprising: (A) forming droplets collectively containing R targets, where R is at least three, and where a significant number of the droplets contain a copy of each of two or more of the targets; (B) amplifying the targets in the droplets; (C) collecting data representing amplification the targets in the droplets, the data being collected in fewer than R optical channels each representing a distinct waveband of emitted light; (D) identifying from the data a plurality of droplet populations, wherein forming, amplifying, and collecting are performed such that each droplet population positive for two of the targets is at least substantially resolved from each droplet population positive for only one of the targets; and (E) determining a level of each target based in part on one or more droplet populations identified as containing a pair of the targets.

14. A method of performing a multiplexed digital assay, comprising: (A) amplifying R targets in droplets; (B) collecting data representing amplification of the targets in the droplets, the data being collected in a plurality of less than R optical channels each representing a distinct waveband of light; (C) identifying from the data a plurality of droplet populations each containing a different combination of the targets; and (D) determining a level of each target, wherein the step of determining for each target is based on a value for droplet counts obtained from a combination of at least two droplet populations that excludes at least two other droplet populations.

15. The method of paragraph 14, wherein one of the plurality of droplet populations contains none of the targets.

16. The method of paragraph 14, wherein one of the plurality of droplet populations contains a copy of each of the targets.

17. A method of performing a digital assay, comprising: (A) forming droplets that collectively contain R targets and a reporter corresponding to each target, wherein R is at least three and each reporter includes a different luminophore; (B) amplifying the targets in the droplets; (C) collecting data representing amplification of the targets in the droplets, the data being collected in less than R optical channels each representing a distinct waveband of light; and (D) determining a level of each target based on the data.

18. The method of paragraph 17, wherein at least one of the reporters reports amplification of the targets in a pair of the optical channels.

19. The method of paragraph 18, wherein at least two of the reporters report amplification of the targets in a pair of the optical channels.

20. The method of paragraph 19, wherein each of the reporters reports amplification of the targets in a pair of the optical channels.

21. The method of paragraph 17, wherein at least one of the reporters reports amplification of the targets in only one of the optical channels.

22. The method of paragraph 17, wherein data representing amplification of the targets is collected in only two optical channels.

23. The method of paragraph 17, further comprising a step of identifying from the data a plurality of droplet populations each containing a different combination of the targets, wherein forming, amplifying, and collecting are performed such that each droplet population positive for two of the targets is at least substantially resolved from each droplet population positive for only one of the targets.

24. The method of any preceding paragraph, wherein the step of determining is based on at least R+2 identified droplet populations.

25. The method of paragraph 24, wherein the step of determining is based on at least 2R identified droplet populations.

26. The method of any preceding paragraph, wherein the droplets are all formed from the same bulk phase.

27. The method of any preceding paragraph, wherein the plurality of droplet populations include a plurality of droplet populations that are each positive for a different pair of the targets.

28. The method of any preceding paragraph, wherein the step of determining for at least one of the targets is based on a value that represents a sum of droplet counts from only one-half of the droplet populations.

29. The method of paragraph 28, wherein the step of determining for each target is based on a value that represents a sum of droplet counts from only one-half of the droplet populations.

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in applications claiming priority from this or a related application. Such claims, whether directed to a different invention or to the same invention, and whether broader, narrower, equal, or different in scope to the original claims, also are regarded as included within the subject matter of the inventions of the present disclosure. Further, ordinal indicators, such as first, second, or third, for identified elements are used to distinguish between the elements, and do not indicate a particular position or order of such elements, unless otherwise specifically stated.

We claim:

1. A method of performing a multiplexed digital assay, the method comprising:
    forming partitions that collectively contain R targets;
    amplifying the R targets in the partitions;
    collecting data representing amplification of each of the R targets in the partitions, all of the data being collected in fewer than R optical channels; and
    determining a respective level of each of the R targets from the data, wherein each level is specific for a single target of the R targets, and wherein the level determined for at least one of the R targets is based in part on a partition count for a partition population positive for two of the R targets;
    wherein the step of determining is based on at least R+2 identified partition populations.

2. The method of claim 1, wherein R is at least three.

3. The method of claim 1, wherein the data is collected in only two optical channels.

4. The method of claim 1, wherein each optical channel represents a different waveband of emitted light.

5. The method of claim 1, wherein each optical channel represents a different waveband of excitation light.

6. The method of claim 1, wherein a different plurality of the partitions contains each different pair of the R targets.

7. The method of claim 1, wherein at least 10% of the partitions contain a pair of the R targets.

8. The method of claim 1, further comprising a step of identifying from the data a plurality of partition populations each positive for a different combination of the R targets.

9. The method of claim 1, wherein the step of determining is based on at least 2R identified partition populations.

10. The method of claim 8, wherein the step of identifying includes a step of resolving each partition population that is positive for exactly two of the R targets from each partition population that is positive for only one of the R targets.

11. A method of performing a multiplexed digital assay, the method comprising:
    forming partitions that collectively contain R targets;
    amplifying the R targets in the partitions;
    collecting data representing amplification of each of the R targets in the partitions, all of the data being collected in fewer than R optical channels;
    identifying from the data a plurality of partition populations each positive for a different combination of the R targets, wherein the step of identifying includes a step of resolving each partition population that is positive for exactly two of the R targets from each partition population that is positive for only one of the R targets; and
    determining a respective level of each of the R targets from the data, wherein each level is specific for a single target of the R targets, and wherein the level determined for at least one of the R targets is based in part on a partition count for a partition population positive for two of the R targets.

12. The method of claim 11, wherein R is at least three.

13. The method of claim 11, wherein the data is collected in only two optical channels.

14. The method of claim 11, wherein each optical channel represents a different waveband of emitted light.

15. The method of claim 11, wherein a different plurality of the partitions contains each different pair of the R targets.

16. The method of claim 11, wherein at least 10% of the partitions contain a pair of the R targets.

17. The method of claim 11, wherein the step of determining is based on at least 2R identified partition populations.

18. A method of performing a multiplexed digital assay, the method comprising:
    forming partitions that collectively contain R targets;
    amplifying the R targets in the partitions;
    collecting data representing amplification of each of the R targets in the partitions, all of the data being collected in fewer than R optical channels, wherein each optical channel represents a different waveband of excitation light; and
    determining a respective level of each of the R targets from the data, wherein each level is specific for a single target of the R targets, and wherein the level determined for at least one of the R targets is based in part on a partition count for a partition population positive for two of the R targets.

19. A method of performing a multiplexed digital assay, the method comprising:
    forming partitions that collectively contain R targets;
    amplifying the R targets in the partitions;
    collecting data representing amplification of each of the R targets in the partitions, all of the data being collected in fewer than R optical channels;
    plotting the data such that partition populations containing different combinations of the R targets form a rectangular array, wherein the step of plotting is performed with respect to a pair of orthogonal axes, and wherein each partition population that is positive for only one of the R targets is arranged along a line that is at least generally parallel to one of the axes; and
    determining a respective level of each of the R targets from the data, wherein each level is specific for a single target of the R targets, and wherein the level determined for at least one of the R targets is based in part on a partition count for a partition population positive for two of the R targets.

20. The method of claim 19, wherein R is at least three.

21. The method of claim 19, wherein the data is collected in only two optical channels.

22. The method of claim 19, wherein each optical channel represents a different waveband of emitted light.

23. The method of claim 19, wherein a different plurality of the partitions contains each different pair of the R targets.

24. The method of claim 19, wherein at least 10% of the partitions contain a pair of the R targets.

25. The method of claim 19, further comprising a step of identifying from the data a plurality of partition populations each positive for a different combination of the R targets.

26. The method of claim 25, wherein the step of identifying includes a step of resolving each partition population that is positive for exactly two of the R targets from each partition population that is positive for only one of the R targets.

27. The method of claim 19, wherein the step of determining is based on at least 2R identified partition populations.

28. The method of claim 19, wherein the array is composed of a plurality of rows and columns, with each row and each column including at least two of the partition populations.

* * * * *